(12) United States Patent
Dewey et al.

(10) Patent No.: US 8,425,608 B2
(45) Date of Patent: Apr. 23, 2013

(54) LORDOTIC EXPANDING VERTEBRAL BODY SPACER

(75) Inventors: Jonathan Dewey, Sunnyvale, CA (US); Marco D. Capote, Lafayette, CO (US); Eric Potts, Indianapolis, IN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1495 days.

(21) Appl. No.: 12/016,662

(22) Filed: Jan. 18, 2008

(65) Prior Publication Data

US 2009/0187248 A1    Jul. 23, 2009

(51) Int. Cl.
*A61F 2/44* (2006.01)

(52) U.S. Cl.
USPC ...................................................... 623/17.16

(58) Field of Classification Search ................ 623/17.15, 623/17.16
See application file for complete search history.

(56) References Cited

U.S. PATENT DOCUMENTS

| | | |
|---|---|---|
| 4,157,715 A | 6/1979 | Westerhoff |
| 4,401,112 A | 8/1983 | Rezaian |
| 4,657,550 A | 4/1987 | Daher |
| 4,820,305 A | 4/1989 | Harms |
| 4,932,975 A | 6/1990 | Main et al. |
| 5,026,373 A | 6/1991 | Ray et al. |
| 5,062,850 A | 11/1991 | MacMillan et al. |
| 5,281,226 A | 1/1994 | Davydov et al. |
| 5,336,223 A | 8/1994 | Rogers |
| 5,571,190 A | 11/1996 | Ulrich et al. |
| 5,571,192 A | 11/1996 | Schonhoffer |
| 5,702,451 A | 12/1997 | Biedermann |
| 5,702,453 A | 12/1997 | Rabbe et al. |
| 5,702,455 A | 12/1997 | Saggar |
| 5,723,013 A | 3/1998 | Jeanson et al. |
| 5,776,197 A | 7/1998 | Rabbe et al. |
| 5,776,198 A | 7/1998 | Rabbe et al. |
| 5,989,290 A | 11/1999 | Biedermann et al. |
| 6,015,436 A | 1/2000 | Schonhoffer |
| 6,086,613 A | 7/2000 | Camino et al. |
| 6,159,244 A | 12/2000 | Suddaby |

(Continued)

FOREIGN PATENT DOCUMENTS

| | | |
|---|---|---|
| DE | 4012622 C1 | 7/1991 |
| DE | 19509317 A1 | 9/1996 |

(Continued)

OTHER PUBLICATIONS

International Search Report, Jun. 1, 2009.

*Primary Examiner* — Kevin T Truong
*Assistant Examiner* — David Bates

(57) ABSTRACT

An expandable medical implant for supporting bone structures includes a curved outer member to cooperatively engage a first bone structure and a curved inner member configured to cooperatively engage a second bone structure. The curved inner member is receivable within and movable relative to the curved outer member along an arc bounded by the curvature of the curved outer member. One of the curved outer and inner members may include a tapered surface and the other of the curved outer and inner members may include a scalloped surface. The implant may include a locking element disposed between the tapered and scalloped surface. The locking element is movable between a locked position engaging the tapered surface and a roughened locking surface to inhibit a decrease in the overall height of the implant and an unlocked position permitting at least an increase in the overall height of the implant.

15 Claims, 19 Drawing Sheets

U.S. PATENT DOCUMENTS

| | | |
|---|---|---|
| 6,176,881 B1 | 1/2001 | Schar et al. |
| 6,190,413 B1 | 2/2001 | Sutcliffe |
| 6,193,755 B1 | 2/2001 | Metz-Stavenhagen et al. |
| 6,193,756 B1 | 2/2001 | Studer et al. |
| 6,200,348 B1 | 3/2001 | Biedermann et al. |
| 6,296,665 B1 | 10/2001 | Strnad et al. |
| 6,332,895 B1 | 12/2001 | Suddaby |
| 6,344,057 B1 | 2/2002 | Rabbe et al. |
| 6,352,556 B1 | 3/2002 | Kretschmer et al. |
| 6,395,034 B1 | 5/2002 | Suddaby |
| 6,454,806 B1 | 9/2002 | Cohen et al. |
| 6,524,341 B2 | 2/2003 | Lang et al. |
| 6,562,074 B2 | 5/2003 | Gerbec et al. |
| 6,616,695 B1 | 9/2003 | Crozet et al. |
| 6,648,917 B2 | 11/2003 | Gerbec et al. |
| 6,719,796 B2 | 4/2004 | Cohen et al. |
| 6,866,682 B1 | 3/2005 | An et al. |
| 6,991,653 B2 | 1/2006 | White et al. |
| 7,156,874 B2 | 1/2007 | Paponneau et al. |
| 7,544,208 B1 * | 6/2009 | Mueller et al. ............. 623/17.15 |
| 2002/0161441 A1 | 10/2002 | Lang et al. |
| 2003/0163199 A1 | 8/2003 | Boehm et al. |
| 2003/0181980 A1 | 9/2003 | Berry et al. |
| 2003/0191531 A1 | 10/2003 | Berry et al. |
| 2003/0208272 A1 | 11/2003 | Crozet et al. |
| 2004/0073314 A1 | 4/2004 | White et al. |
| 2004/0153160 A1 | 8/2004 | Carrasco |
| 2004/0186569 A1 | 9/2004 | Berry |
| 2005/0060034 A1 | 3/2005 | Berry et al. |
| 2005/0090898 A1 | 4/2005 | Berry et al. |
| 2005/0096744 A1 | 5/2005 | Trieu et al. |
| 2005/0113921 A1 | 5/2005 | An et al. |
| 2005/0159814 A1 | 7/2005 | Karahalios |
| 2005/0187634 A1 | 8/2005 | Berry |
| 2005/0209697 A1 | 9/2005 | Paponneau et al. |
| 2005/0234550 A1 | 10/2005 | Metz-Stavenhagen |
| 2006/0058879 A1 | 3/2006 | Metz-Stavenhagen |
| 2006/0116770 A1 | 6/2006 | White et al. |
| 2007/0123987 A1 * | 5/2007 | Bernstein ................... 623/17.11 |
| 2007/0270964 A1 * | 11/2007 | Strohkirch et al. ......... 623/17.11 |
| 2008/0114467 A1 * | 5/2008 | Capote et al. .............. 623/23.47 |

FOREIGN PATENT DOCUMENTS

| | | |
|---|---|---|
| DE | 19804765 A1 | 9/2000 |
| DE | 20213013 U1 | 1/2003 |
| EP | 0490159 A1 | 6/1992 |
| EP | 1080703 A2 | 3/2001 |
| EP | 1188424 A1 | 3/2002 |
| FR | 2636227 A1 | 11/2007 |
| WO | WO9201428 A1 | 2/1992 |
| WO | 9808468 | 3/1998 |
| WO | WO9846173 A1 | 10/1998 |
| WO | WO9939665 A1 | 8/1999 |
| WO | WO9963913 A2 | 12/1999 |
| WO | WO0023013 A1 | 4/2000 |
| WO | WO0045751 A1 | 8/2000 |
| WO | WO02071986 A2 | 9/2002 |
| WO | WO03096937 A1 | 5/2003 |
| WO | WO2004089256 A1 | 10/2004 |
| WO | 2004100837 A1 | 11/2004 |
| WO | 2007137022 A2 | 11/2007 |

* cited by examiner

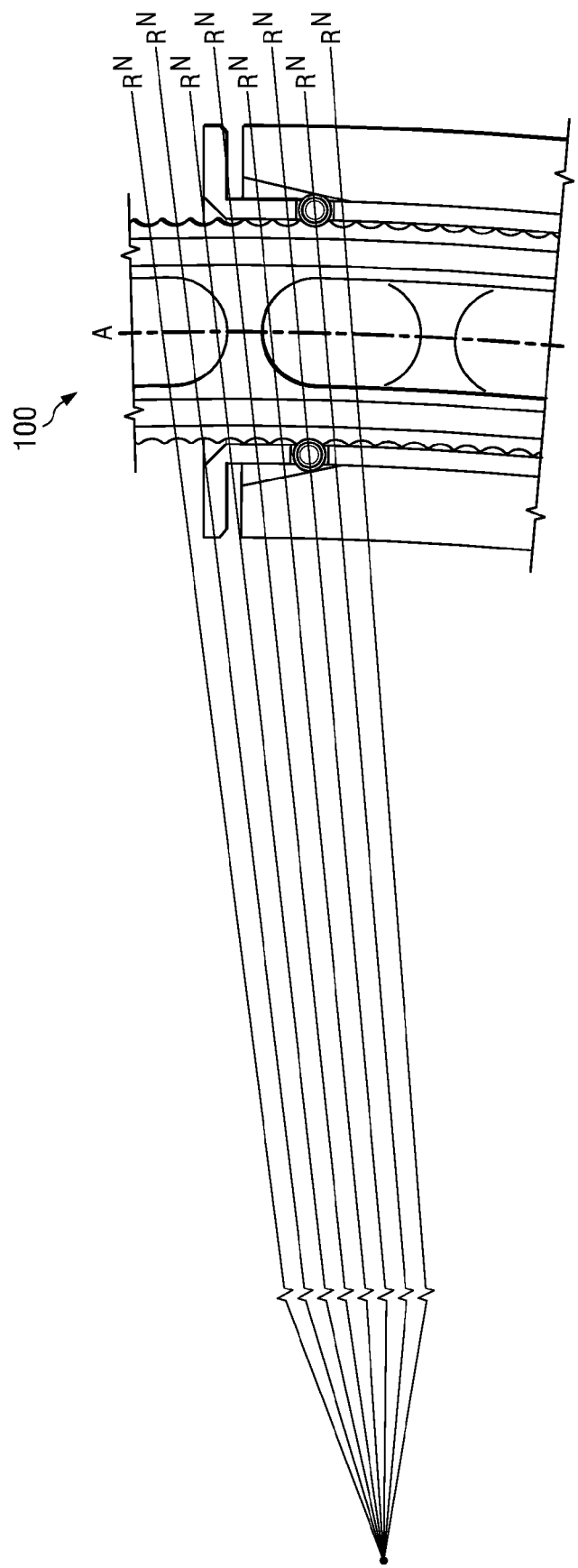

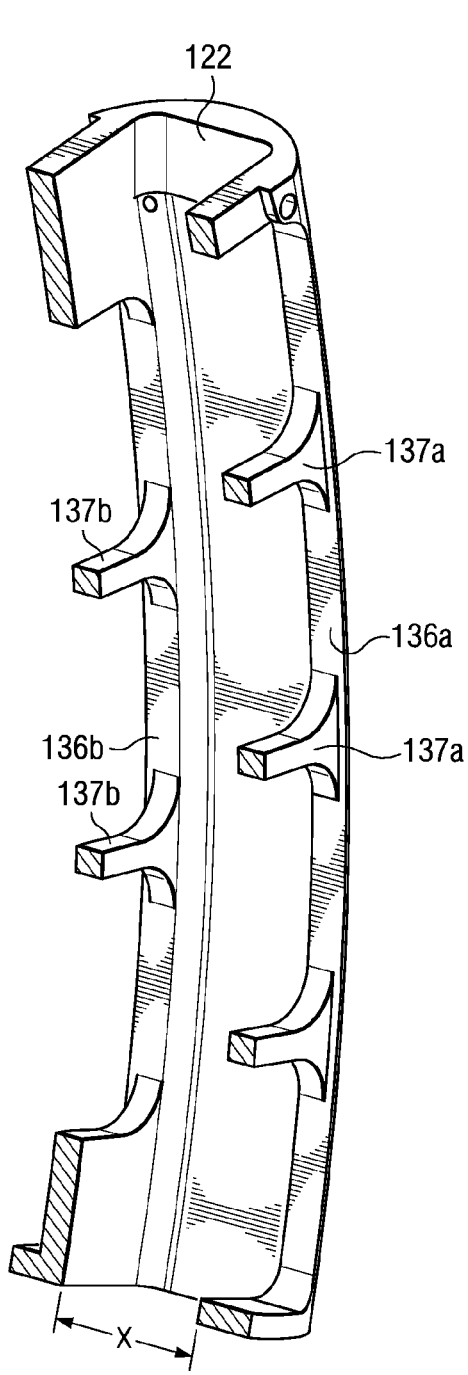
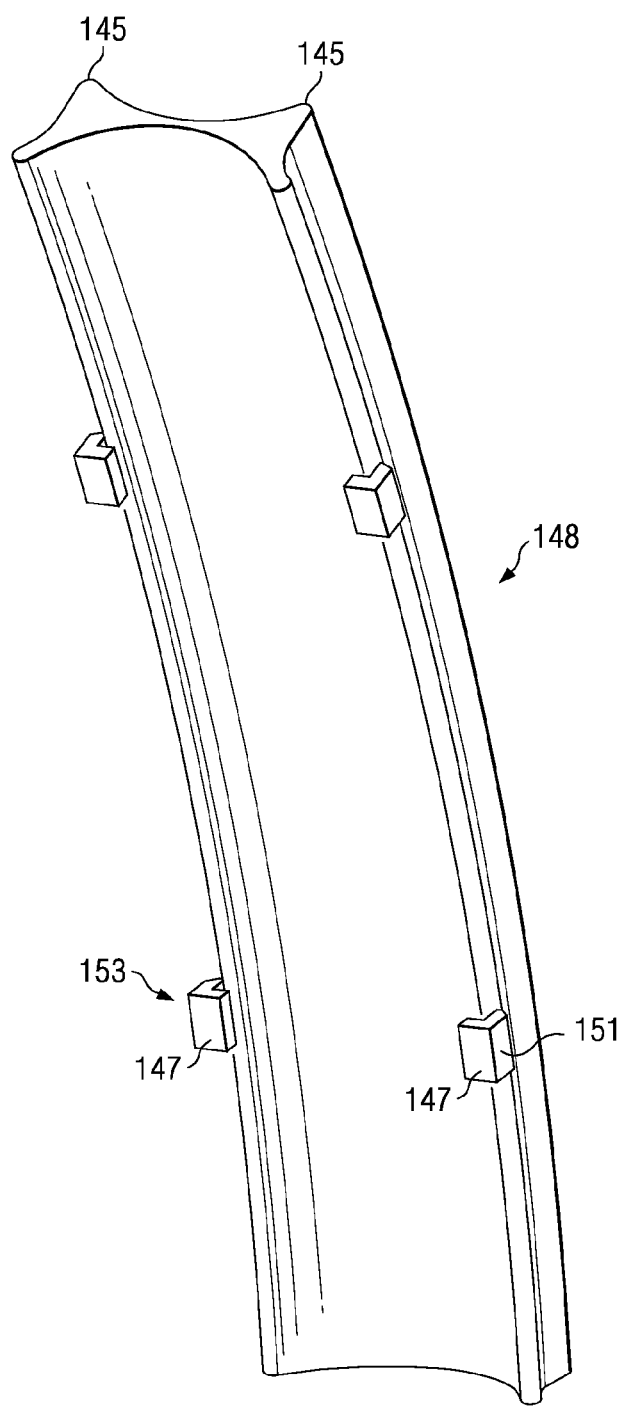
Fig. 20
Fig. 21

LORDOTIC EXPANDING VERTEBRAL BODY SPACER

FIELD OF THE INVENTION

The present invention relates generally to the field of medical implants, and more particularly relates to an expandable implant and method for replacing bone structures such as one or more vertebrae or long bones.

BACKGROUND

It is sometimes necessary to remove one or more vertebrae, or a portion of the vertebrae, from the human spine in response to various pathologies. For example, one or more of the vertebrae may become damaged as a result of tumor growth or may become damaged by a traumatic or other event. Excision of at least a generally anterior portion, or vertebral body, of the vertebra may be referred to as a corpectomy. An implant is usually placed between the remaining vertebrae to provide structural support for the spine as a part of a corpectomy. FIG. 1 illustrates four vertebrae, V1-V5 of a typical lumbar spine and four spinal discs, D1-D4. As illustrated, V2-V4 are damaged vertebrae and all or a part of V2-V4 could be treated by removing them from the spine. If removed along with spinal discs D1-D4, an implant may be placed between vertebrae V1 and V5 as seen in FIG. 1A to help stabilize the spine. Most commonly, the implant inserted between the vertebrae is designed to facilitate fusion between remaining vertebrae. Sometimes the implant is designed to replace the function of the excised vertebra and discs. All or part of more than one vertebrae may be damaged and require removal and replacement in some circumstances.

Many implants are known in the art for use in a corpectomy procedure. One class of implants is sized to directly replace the vertebra or vertebrae that are being replaced. Another class of implants is inserted into the body in a collapsed state and then expanded once properly positioned. Expandable implants may be advantageous because they allow for a smaller incision when properly positioning an implant. Additionally, expandable implants may assist with restoring proper loading to the anatomy and achieving more secure fixation of the implant. Implants that include insertion and expansion members that are narrowly configured may also provide clinical advantages. In some circumstances, it is desirable to have vertebral endplate contacting surfaces that effectively spread loading across the vertebral endplates. Some effective implants also may include a member for maintaining the desired positions, and in some situations, being capable of collapsing. Fusion implants with an opening may also be advantageous because they allow for vascularization and bone growth through all or a portion of the entire implant. This disclosure includes devices and methods that address one or more deficiencies in the prior art.

SUMMARY

In one exemplary aspect, this disclosure is directed toward an expandable medical implant for supporting bone structures is disclosed. The implant has an overall curved shape relative to and extending along a longitudinal axis. The implant may include a curved outer member configured to cooperatively engage a first bone structure and a curved inner member receivable in the curved outer member. In addition, the curved inner member may be configured to cooperatively engage a second bone structure. The curved inner member may be movable relative to the curved outer member along an arc bounded by the curvature of the curved outer member thereby increasing or decreasing the overall height of the implant. One of the curved outer and inner members may include a tapered surface and the other of the curved outer and inner members may include a scalloped surface. The implant may also include a locking element disposed between the tapered surface and the scalloped surface. The locking element may be movable between a locked position engaging the tapered surface and a roughened locking surface to inhibit a decrease in the overall height of the implant and an unlocked position permitting at least an increase in the overall height of the implant.

In another exemplary aspect, a curved locking member may be disposed between the curved inner and outer members. The locking member may include a locking element receiver aperture containing the locking element, and may be configured to act on the locking element to affect the position of the locking element relative to the outer member. The tapered surface of the outer member may be configured to affect the position of the locking element relative to the scalloped surface of the inner member.

In another exemplary aspect, an expandable prosthesis for implantation between bone structures is disclosed. The expandable prosthesis has an overall curved shape relative to a longitudinal axis. The expandable prosthesis may have a first expandable implant having a first outer curved member and a first inner curved member where the first expandable implant is configured to cooperatively engage a first bone structure. The first inner curved member may be receivable within the first outer curved member and movable relative to the first outer curved member along an arc bounded by the first outer curved member. The first expandable implant may further comprise a first locking curved member disposed between the first inner curved member and the first outer curved member to limit the movement of the first inner curved member relative to the first outer curved member. The expandable prosthesis may have a second expandable implant configured to cooperatively interface with the first expandable implant and configured to cooperatively engage a second bone structure.

In yet another exemplary aspect, a method of supporting vertebra with an expandable medical implant is disclosed. The method may include gaining surgical access to a curved portion of the spinal column and removing one or more damaged vertebras to form a vertebral gap. The method may also include providing a supporting implant having an inner curved member and an outer curved member with an adjustable locking mechanism therebetween. The locking mechanism may be movable between an unlocked position allowing the inner curved member to move relative to the outer curved member and a locked position inhibiting movement. The supporting implant may be placed between vertebrae to be supported and the inner curved member may be displaced relative to the outer curved member to a height approximating the natural height of the vertebral gap. The locking mechanism may be moved to the locked position to retain the height of the supporting implant, and the supporting implant may be positioned in the spinal column oriented to approximate the height and curvature of the one or more removed vertebra.

In another exemplary aspect, an expandable prosthesis for implantation between bone structures is disclosed. The expandable prosthesis has an overall curved shape relative to a longitudinal axis. The expandable prosthesis may have an outer member having a first end surface defining a first plane with the first end surface being configured to cooperatively engage a first bone structure. The first expandable implant may further comprise an inner member having a second end surface defining a second plane with the second end surface being configured to cooperatively engage a second bone structure. The inner member may be receivable within the outer member and movable relative to the outer member along a curved path between a first position and a second position wherein the second position is an expanded position. The second plane intersects the first plane at a first angle when the inner member is in the first position and the second plane intersects the first plane at a second angle when the inner member is in the second position. The expandable prosthesis may further comprise a locking member disposed between the outer and inner members having a flange and locking element with the locking element being movable relative to the outer and inner members between a locked position that inhibits an increase in the first angle and an unlocked position permitting an increase from at least the first angle to the second angle.

In yet another exemplary aspect, a method of forming a lumen within a medical implant is disclosed. The method may include positioning an end mill at a first side of the implant and cutting the first side of the implant with the end mill to form a plurality of first apertures with a first depth wherein the first apertures are separated by a support bar. The method may include positioning the end mill at an opposing second side of the implant and cutting the second side of the implant with the end mill to form at least one second aperture wherein the second aperture is spaced to overlap with more than one of the first apertures and spaced to overlap the support bar. The second aperture has a depth forming an inner surface of the support bar, such that the cutting depth of the plurality of first apertures and the cutting depth of the second aperture overlap to form a lumen within the implant.

Further aspects, forms, embodiments, objects, features, benefits, and advantages of the present invention shall become apparent from the detailed drawings and descriptions provided herein.

BRIEF DESCRIPTION OF THE DRAWINGS

FIG. 8C is an illustration of another exemplary post component showing a roller and scallop.

FIG. 20 is a sectional pictorial illustration of the base component of FIG. 4A taken along line 20-20 in FIG. 4A showing the formation of the bore within the base component.

FIG. 21 is an isometric pictorial illustration of an exemplary guard component that may be attached to the implant of FIG. 2.

DETAILED DESCRIPTION

Figure 1:
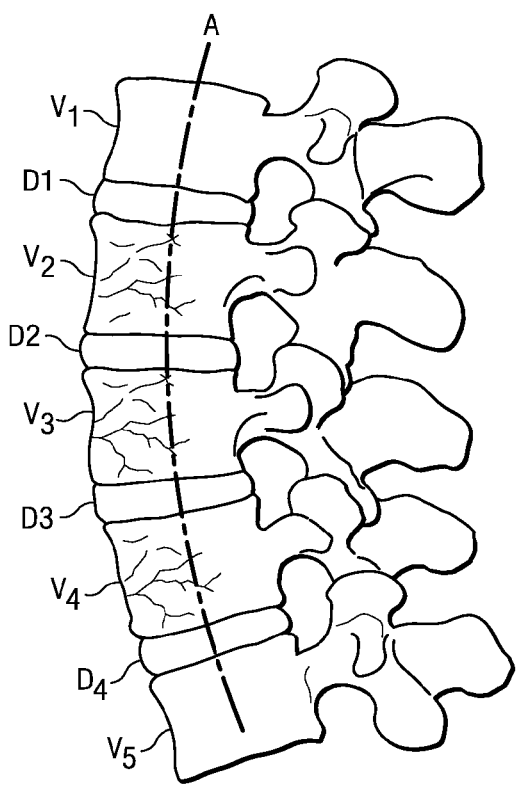
FIG. 1 is an illustration of an elevation view of a segment of a lumbar spine.

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Figure 2:
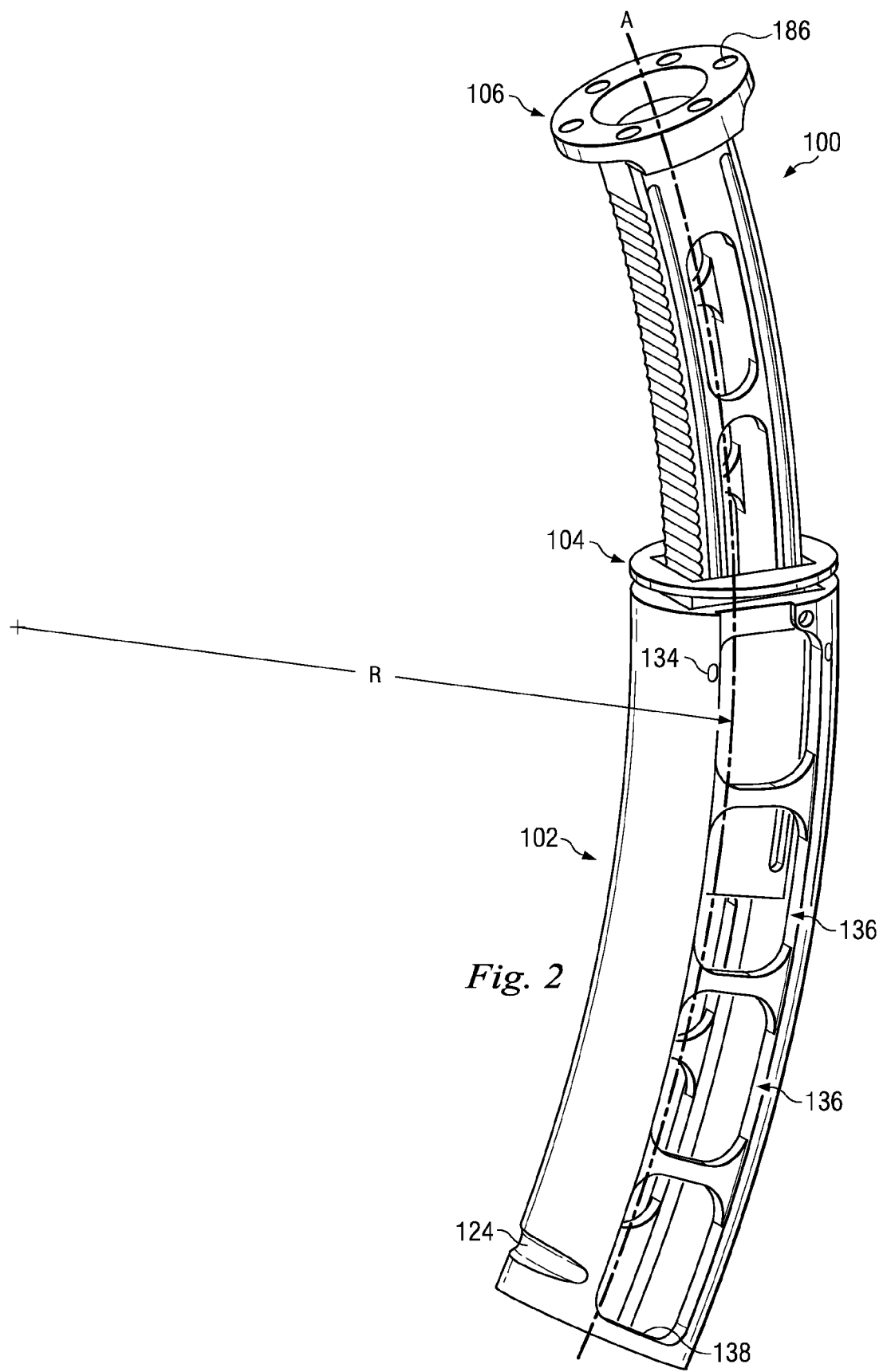
FIG. 2 is a pictorial illustration of an exemplary expandable implant according to one embodiment of the present invention.
Figure 3A:
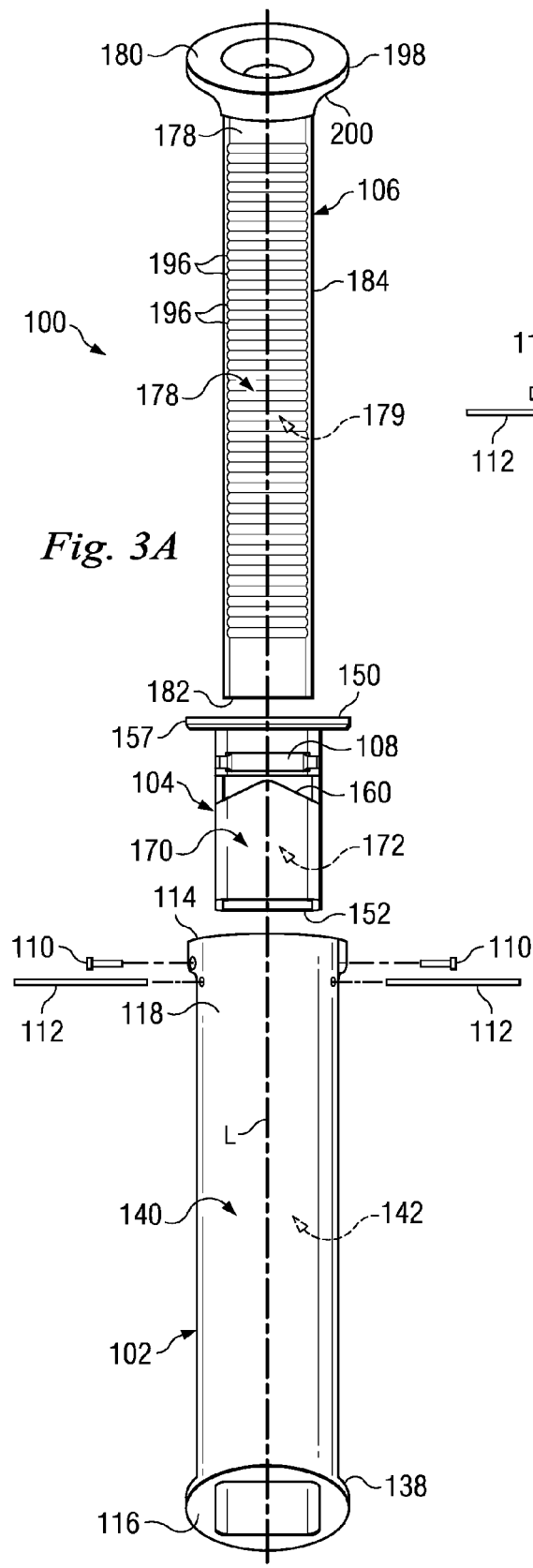
FIGS. 3A-3C are pictorial illustrations of exploded views of the implant of FIG. 2.
Figure 3B:
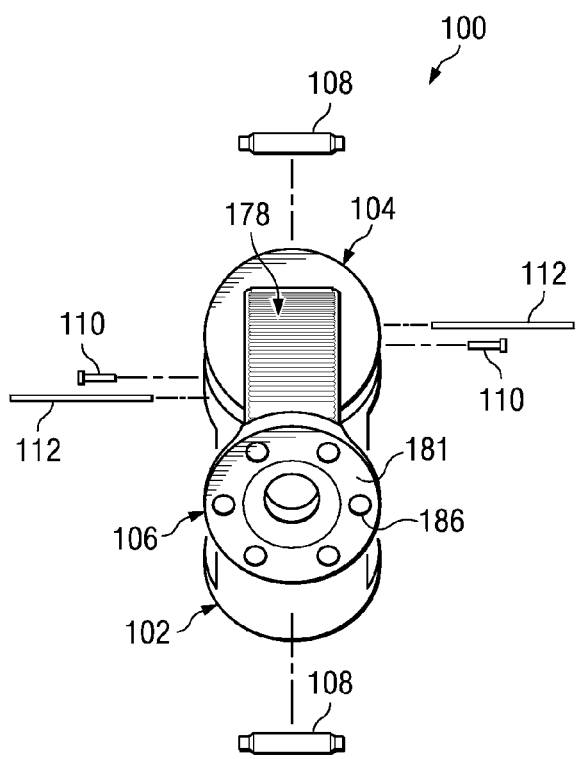
Figure 3C:
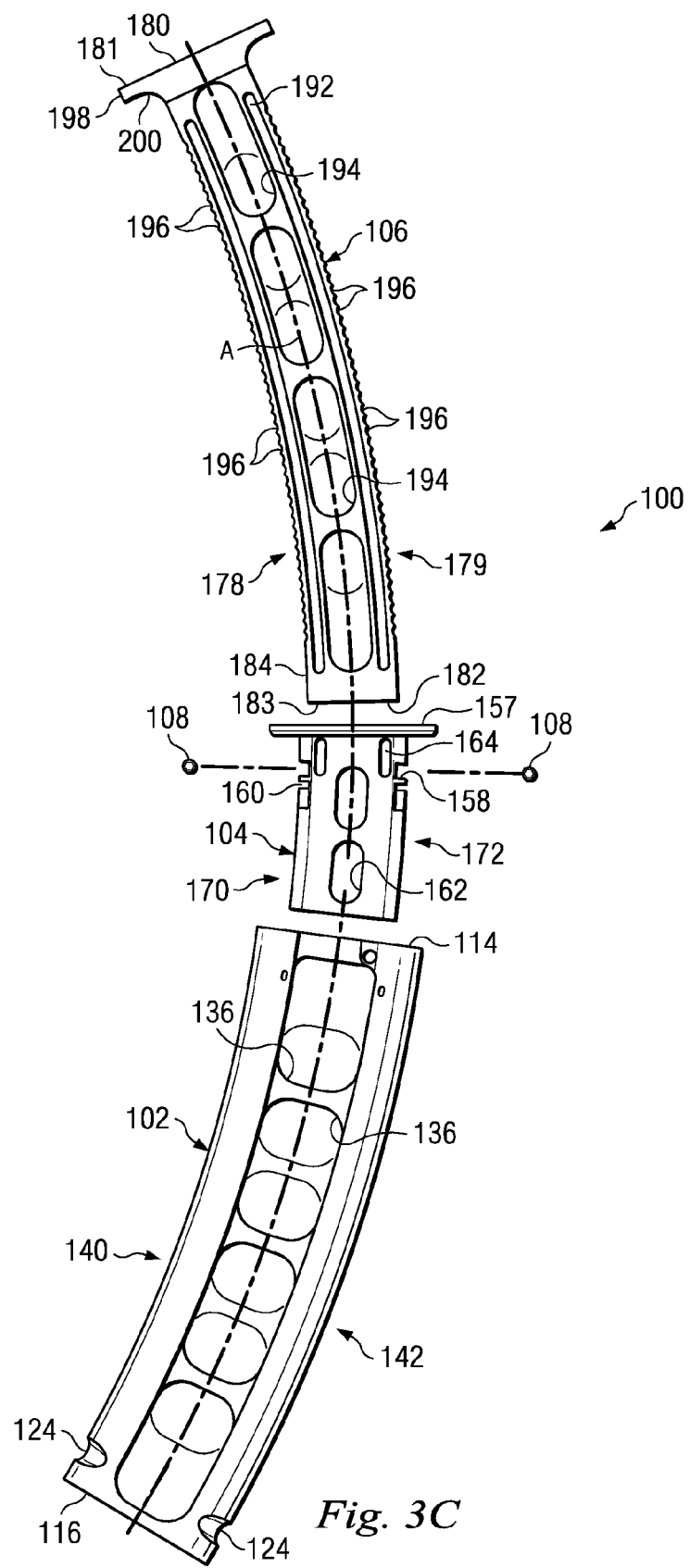

FIGS. 2 and 3A-3C show an exemplary expandable implant 100 usable to secure and space adjacent bone structures. In FIG. 2, the implant 100 is shown fully assembled, while FIGS. 3A-3C show the implant 100 in an exploded condition. Referring to these figures, the implant 100 includes three main components including an outer member or base 102, a locking member or locker 104, and an inner member or post 106. In addition to these components, the exemplary implant 100 includes locking elements 108, pegs 110, and biasing elements 112. These components operate together to provide the support and spacing between the adjacent bone structures. More specifically, the base 102, locker 104, and post 106 are curve-shaped to allow implant 100 to have an overall curved shape to provide intervertebral support that more closely matches the natural curvature of the spine. Because of the overall curvature of expandable implant 100 it has a radius of curvature R that extends to the midline of implant 100 as can best be seen in FIG. 2. To be described more in detail below, when implant 100 expands it does so along arc A that is substantially defined by the radius of curvature R.

In the exemplary embodiment shown in FIGS. 2 and 3A-3C, the base 102 is configured and shaped to receive and house the locker 104, which, in turn, is configured and shaped to receive and house the post 106. The locking elements 108 cooperate with the locker 104 to control displacement of the post 106 relative to the base 102, thereby controlling the overall expandability of the implant 100 along arc A. In this embodiment, the pegs 110 connect the base 102, the locker 104, and the post 106 into a unitary mechanism. The biasing elements 112 cooperate with the base 102 and the locker 104 to bias the locker 104, and likewise the locking element 108, into a position that selectively locks or secures the post 106 relative to the base 102, thereby hindering the ability of the implant 100 to collapse after implantation. In the embodiments shown, the biasing element 112 is a leaf spring. However, the biasing element could be any type of spring, including a coil spring, or a material, such as a silicone or elastomeric bumper, or an elastic member, such as a stretchable band that may act in compression or tension.

Figure 4A:
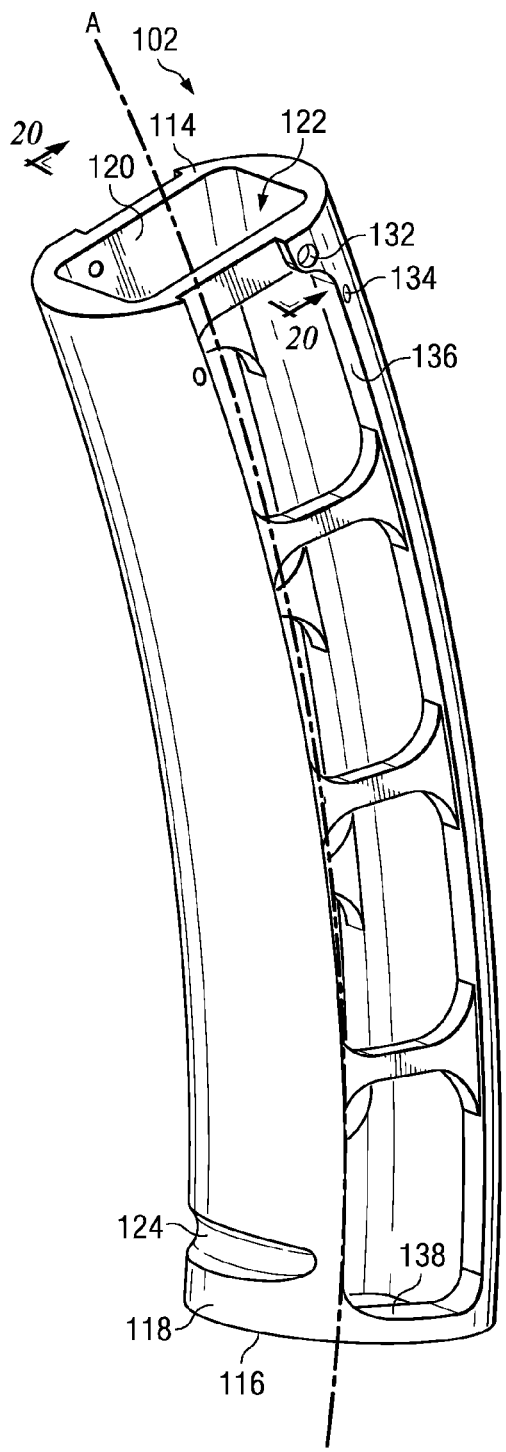
FIG. 4A is an isometric pictorial illustration of an exemplary base component of the implant of FIG. 2.
Figure 6:
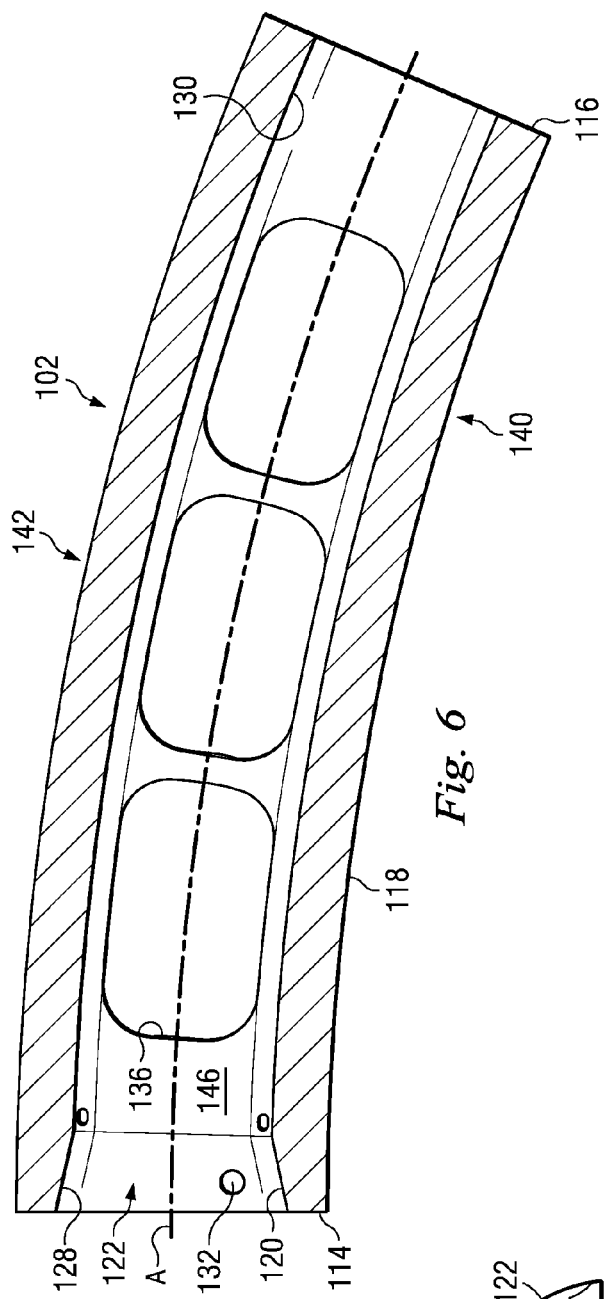
FIG. 6 is a sectional pictorial illustration of the base component of FIG. 5, taken along line 6-6.

The components of the exemplary implant 100 will be described in further detail with reference to FIGS. 4-12. The base 102 will be described first, with reference to FIGS. 4-6, as well as FIGS. 3A-3C. FIG. 4A shows an isometric view of the base 102; FIG. 5 shows a top view; and FIG. 6 shows a cross-sectional view.

The base 102 includes a top surface 114, a bottom surface 116, a concave side 140 formed by outer wall 118 and an inner wall 120, a convex side 142 formed by outer wall 118 and inner wall 120, and a bore 122 defined by the inner wall 120. The outer and inner walls are curved to from a convex side 142 and a concave side 140. The top and bottom surfaces 114, 116 may be relatively flat surfaces having the bore 122 formed therein. The top surface 114 may be configured to cooperate with locker 104, and the bottom surface 116 may be configured to cooperatively engage a bone structure, either directly or through additional components, such as endplates. The bottom surface 116 may include features for attachment to endplates or other components. In some examples, the bottom surface may include features permitting it to attache to additional implants 100, such as for example, another expandable implant similar to the expandable implant 100 disclosed herein. Some of these exemplary features are described below with respect to the post 106.

In the exemplary embodiment shown in FIG. 3, the base 102 is curve-shaped by having concave side 140 that is located on an opposing side of the mid-line shown by arc A from convex side 142 as it extends along the mid-line of arc A. The concave side 140 has a generally concave curvature. The convex side 142 has a generally convex curvature and has a length along the mid-line that is longer than a length of the concave side 140 extending along mid-line A. Although, the exemplary embodiment shows the concave side 140 with a concave curvature and the convex side 142 with a convex curvature, it should be understood that other shapes and dimensions that provide a generally concave or generally convex also are contemplated and are encompassed within the use of the terms "curve", "curved", "concave", and "convex." For example, the terms are intended to include embodiments having, for example, a base with sides formed of a plurality of flat surfaces that are angled with respect to each other at some point between the base's top surface 114 and bottom surface 116 to form a generally concave or generally convex curve shape. In addition, sides 140 and 142 include convexly curved surfaces that extend transverse to the midline shown by arc A.

In the exemplary embodiment shown, the outer wall 118 may include instrument receiving features 124 that cooperate with surgical instruments for placement of the implant 100 between desired bone structures. In the embodiment shown, the instrument receiving features 124 are indentations on opposite sides of the base outer wall 118, however, it is contemplated that many other features could be used to cooperate with instruments that would allow the instruments to grip, support, or otherwise place the implant 100 in a desired location. Further, some embodiments are altogether devoid of any instrument receiving features.

In the exemplary embodiment shown, in addition to the instrument receiving features 124, the outer wall 118 includes additional cutouts and features that function to reduce the mass of the implant 100 while maintaining sufficient strength to properly support the bone structures and weight of a patient. In addition, these additional cutouts and features may simplify additional processing, such as, for example, when using a wire EDM to cut features at the bottom surface 116.

Referring now to FIGS. 5 and 6, the base 102 includes the inner wall 120, forming the bore 122. In this exemplary embodiment, the bore 122 extends from the top surface 114 to the bottom surface 116 along arc A formed by concave side 140 and convex side 142, as best seen in FIG. 6. The bore 122 in this exemplary embodiment is substantially rectangular across the bore opening 144 and substantially curved along the depth of the bore cavity 146. Accordingly, the inner wall 120 may be formed of a concave curvature on concave side 140 and a convex curvature on convex side 142 to form the curved shape of bore cavity 146. It should be noted that in other embodiments, the bore 122 is formed of other polygon shapes, such as, for example, triangular, square, or pentagon. Still other embodiments have bores that are oval or circular shaped. As illustrated in FIG. 2, the bore 122 is configured to receive the locker 104 of the implant 100.

The inner wall 120 has a tapered section 128 and a non-tapered section 130 relative to the arc A. In the exemplary embodiment shown, the tapered section 128 is adjacent the top surface 114 of the base 102, while the non-tapered section 130 is adjacent the bottom surface 116 of the base 102. However, the tapered section 128 may be otherwise arranged or placed. As discussed further below, the tapered section 128 cooperates with the locking element 108 to secure the height of the implant 100 at a desired level. Also, in the exemplary embodiment shown, the inner wall 120 includes two tapered sections 128, disposed on opposite sides of the bore 122. Other embodiments include one or more than two tapered sections, and for the reasons described below, symmetry may provide advantages when expanding the implant 100.

In addition to the elements described, the base 102 also includes a peg aperture 132, a biasing member aperture 134, and a vascularization aperture 136. During assembly, the peg 110 may be inserted into the peg aperture 132, and the biasing element 112 may be inserted through the biasing member aperture 134. The vascularization aperture 136 provides access to the bore 122 and may be used to introduce bone graft, tissue, or other material into the bore 122 after implantation. In addition, it allows fluid into the interior of the base 102, thereby encouraging bone growth. Because of the cutouts, the outer wall 118 of the base 102 also forms a flange 138, as best seen in FIGS. 2, 3A, and 4A.

Figure 4B:
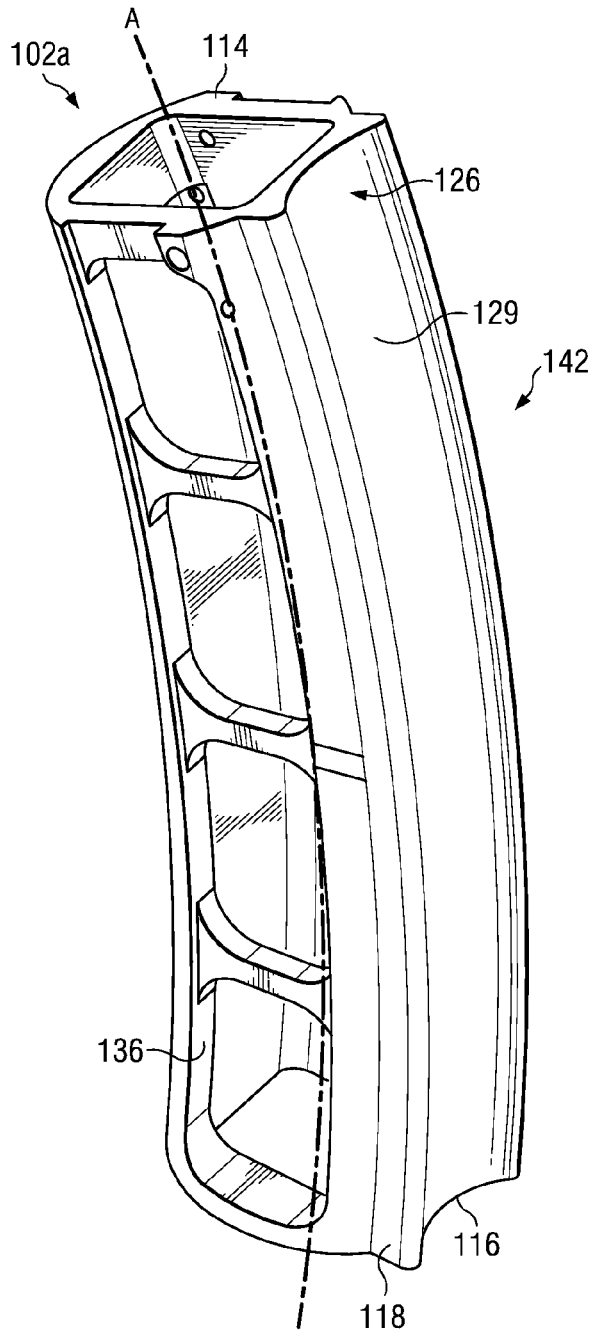
FIG. 4B is an isometric pictorial illustration of another exemplary base component with a trough formed therein that may be usable as a part of the implant in FIG. 2.
Figure 5:
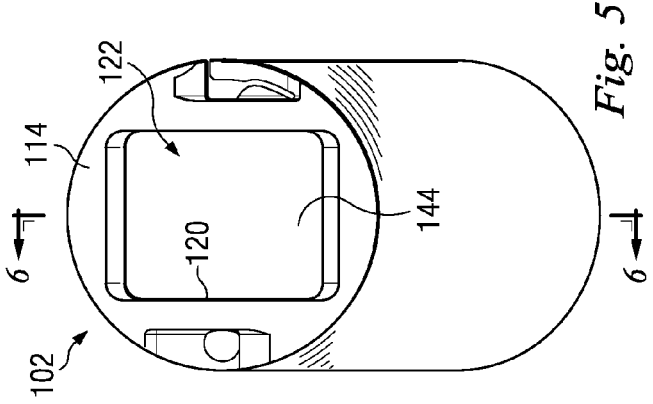
FIG. 5 is a top pictorial illustration of the base component of FIG. 4.

FIG. 4B shows an additional embodiment of a base referenced by the reference numeral 102a. This base 102a includes many of all the features of the base 102 discussed above and in some embodiments may replace base 102 in the implant 100. Further it is contemplated that any feature of either base 102 or base 102a may be used on the other of the base 102 and the base 102a. The base 102a as seen in FIG. 4B, can have a trough 126 with a trough surface 129. The trough 126 may be formed as part of the base's outer wall 118 and may extend from the top surface 114 to the bottom surface 116 on either one of or both of the concave side 140 and convex side 142 of the base 102a. The trough 126 may be shaped to match the contour of the anatomy surrounding the spine. Specifically the trough surface 129 may be smooth and rounded and may be configured to receive or support without damaging surrounding tissue or dura such as, for example, anterior veins or a recipient's spinal cord. Additionally, the trough surface 129 may have a lubricious surface to avoid irritation and damage to the surrounding dura and blood vessels that are present within the spinal region.

As shown in FIG. 2, the base 102 receives the locker 104, which is described with reference to FIGS. 2, 3A-3C, 7A-C. The locker 104 includes an upper end 150, a lower end 152, a concave side 170 formed by an inner surface 154 and an outer surface 156, a convex side 172 formed by the inner surface 154 and the outer surface 156, and a flange 157.

In this exemplary embodiment and as shown in FIGS. 2 and 3A in an assembled condition, the upper end 150 is disposed outside the base 102, and the lower end 152 is disposed within the bore 122 of the base 102. At the upper end 150, the flange 157 radially extends to have an outer perimeter substantially matching that of the base 102. As described below, the flange 157 may be used to displace the locker 104 relative to the base 102 in order to change the overall height of the implant 100 along arc A.

In the exemplary embodiment, the locker 104 is curve-shaped, having the concave side 170 that is located on an opposing side from the convex side 172. The concave side 170 has a generally concave curvature. The convex side 172 has a generally convex curvature and has a length greater than the length of concave side 170. Based on the curvatures and dimensions of the concave side 170 and convex side 172, the outer surface 156 of the locker 104 is sized and formed to be received within the bore 122 of the base 102. In this embodiment, like the bore 122 of the base 102, the outer surface 156 is substantially rectangular across and substantially curved to match the bore opening 144 and the bore cavity 146 of the base 102. However, the outer surface 156 may be in the form of other shapes, as described above with reference to the base 102.

The outer surface 156 includes a locking element receiver 158, which in this embodiment is an aperture from the outer surface 156 to the inner surface 154. In addition, the outer surface includes a biasing member support 160, a vascularization aperture 162, and a peg slot 164.

Figure 7A:
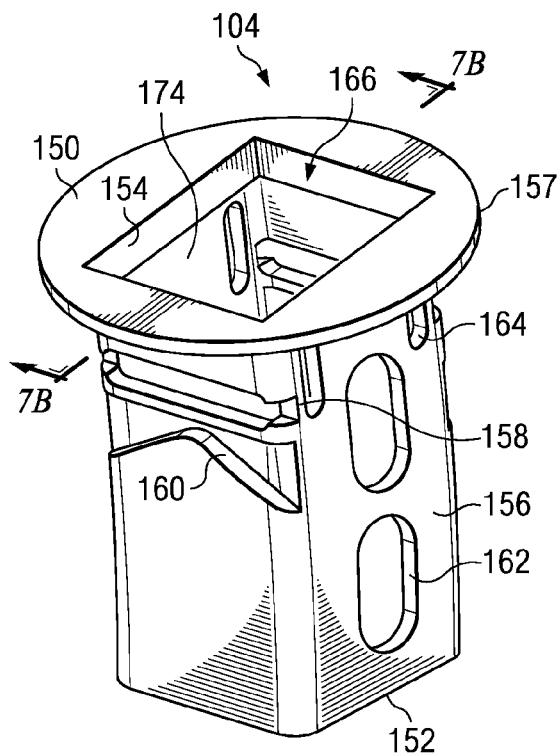
FIG. 7A is an isometric pictorial illustration of an exemplary locker component of the implant of FIG. 2.
Figure 7B:
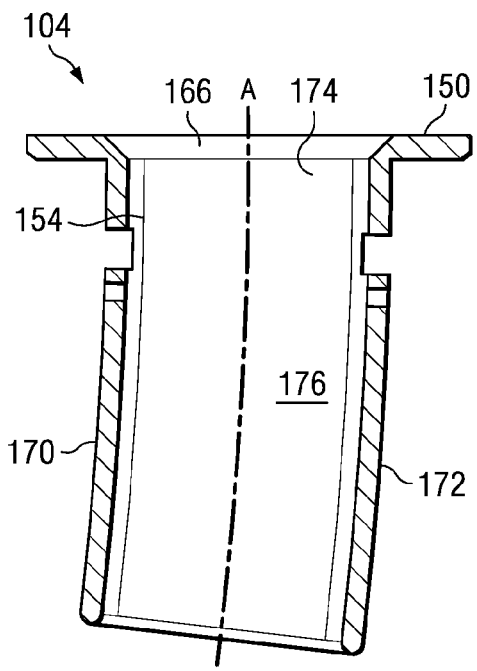
FIG. 7B is a sectional pictorial illustration of the locker component of FIG. 2 taken along line 7B-7B in FIG. 7A.
Figure 7C:
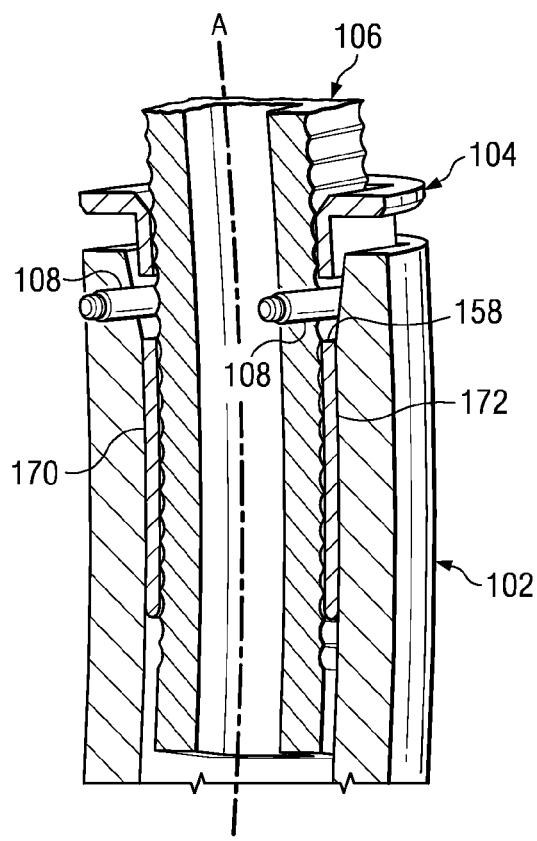
FIG. 7C is an isometric pictorial illustration of an alternative locker component of the implant of FIG. 2.

As described further below, the locking element 108 fits within and extends through the locking element receiver 158 to engage and disengage the base 102 and the post 106, thereby restricting and permitting movement of the post 106 relative to the base 102. As seen in FIGS. 3A, 3C, and 7A, the locking elements 108 and locking element receivers 158 are located on both the concave side 170 and the convex side 172 of locker 104. Other embodiments however, have locking elements 108 and locking element receivers 158 on only one side of the concave and convex sides 170, 172 or alternatively on the surfaces extending between the concave and convex sides 170, 172 are contemplated. Because the locker 108 is curved along an arc A, the distance along the convex side 172 between the upper end 150 of locker 104 to the locking element receiver 158 is greater than the distance along the concave side 170 between the upper end 150 of locker 104 to the locking element receiver 158. An alternative embodiment is shown in FIG. 7C, the locker, referenced herein by reference numeral 104a, includes locking elements and locking element receivers as described above. However, the locking elements and locking element receivers are formed on the sides extending between the concave and convex sides 170, 172. Specifically, the locking element receivers 158 may be located substantially perpendicular to concave side 170 and convex side 172 at an angle substantially normal to the arc A defined by radius of curvature R. In the alternative embodiment shown in FIG. 7C, the distance between the locking element receiver 158 on either side of the locker 104a to the upper end 150 of locker 104a is the same.

The biasing member support 160 cooperates with the biasing member 112 to provide a biasing force on the locker 104 to maintain it within the base 102. The peg slot 164 receives the peg 110, which also extends through the base 102. This allows the locker 104 to move relative to the peg 110, but the peg 110 blocks removal of the locker 104 from the base 102. Accordingly, the peg slot 164 cooperates with the peg 110 to slidably maintain the locker 104 within the base 102.

The inner surface 154 of the locker 104 forms a locker bore 166. The locker bore 166 in this exemplary embodiment extends from the upper end 150 to the lower end 152 along arc A formed by concave side 170 and convex side 172, as best seen in FIG. 7B. The bore 166 in this exemplary embodiment is substantially rectangular across the bore opening 174 and substantially curve-shaped along the bore cavity 176. However, the locker bore 166 could be formed into some other shape. As will be described below, the locker bore 166 is configured and sized to receive the post 106.

The post 106 will be described with reference to FIGS. 8A and 3A-3C. The post 106 includes a top end 180, a bottom end 182, and a main body 184 having a concave side 178 and a convex side 179. The top end 180 includes a top surface 181 having end plate connectors 186 formed therein. In the embodiment shown, the end plate connectors 186 are configured for attachment to an end plate (not shown). In the embodiment shown, the end plate connectors 186 are a series of holes configured to attach to endplates. In some embodiments, instead of attaching to separate endplates, the post 106 is configured to cooperatively attach directly to bone structure. In this exemplary embodiment, one end plate connector 186 may include an attachment aid 188 that cooperates with an end plate to secure the end plate onto the top surface 180 of the post 106. In this embodiment, the attachment aid 188 is a spring feature that is deformable to receive an endplate post and frictionally grip it to hold the endplate in place during implantation. In addition, the bottom surface 116 of the base 102 may include similar features, including the end plate connectors and the attachment aid, such as the spring feature. In some embodiments, the end plate connectors are cylindrical posts that extend from an endplate and are configured to be received by the end plate connectors 186. The end plates could be at any angle or of various types.

In the exemplary embodiment, the post 106 is curve-shaped. The concave side 178 has a generally concave curvature and convex side 179 has a generally convex curvature. Here, as a result of the curved surfaces, the convex side 179 has a length greater than the length of the concave side 178. Based on the curvatures and dimension of concave side 178 and convex side 179, the main body 184 is sized and formed to be received within the locker bore 166, and is slidable relative to the locker 104 and the base 102 along arc A. Specifically, the bottom end 182 of the post 106 is sized and formed to be received within the locker bore 166 and includes a bottom surface 183 having a vascularization aperture 190 formed therein. In this embodiment, like the locker bore 166, the bottom end 182 is substantially rectangular with the main body 184 being substantially curved to match the curved shape of bore cavity 176. However, the bottom end and bore cavity may be in the form of other shapes, as described above with reference to the base 102.

The main body 184 includes a peg slot 192, additional vascularization holes 194, and a locking surface 196. The peg slot 192 is configured to receive the peg 110, which also extends through the base 102 and locker 104. Because of the length of the peg slot 192, the post 106 may be raised or lowered relative to the peg 110 to increase or decrease the overall height of the implant 100. The vascularization holes 194 and the vascularization aperture 190 provides access for placement of bone graft or other material and allows fluid flow to promote bone growth and attachment to the bone structures.

Figure 8A:
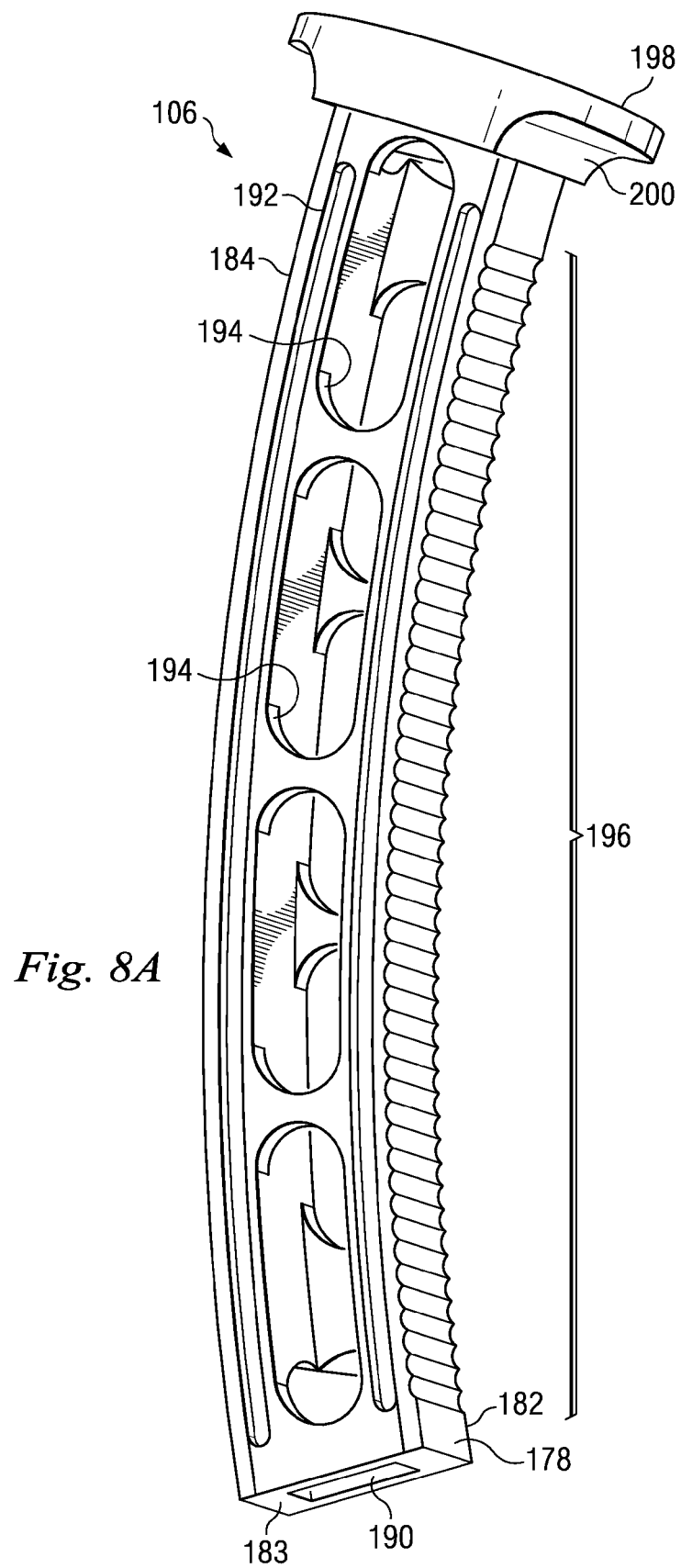
FIG. 8A is an isometric pictorial illustration of an exemplary post component of the implant of FIG. 2.
Figure 8B:
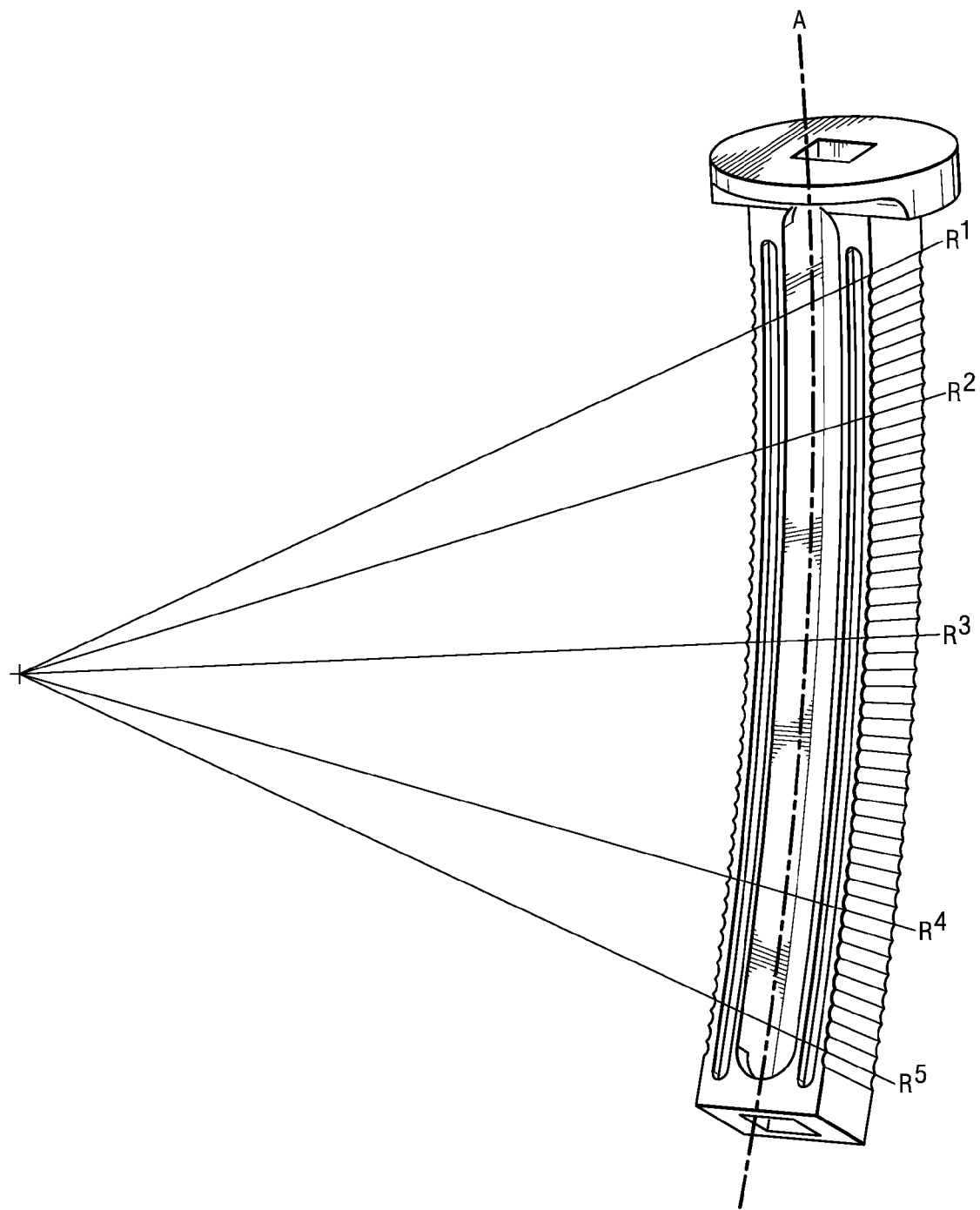
FIG. 8B is an isometric pictorial illustration of an exemplary implant.

The locking surface 196 is the area configured to contact the locking element 108, and in this exemplary embodiment, may include roughened features, such as, for example, a series of roughening scallops along the concave curvature of concave side 178 and the convex curvature of convex side 179 as shown in FIGS. 3C and 8A. FIGS. 8B and 8C show an additional embodiment of an exemplary post 106a. Here the exemplary post 106a includes roughened scallops similar to those on post 106 in FIG. 8A. As seen in FIG. 8B, the roughened scallops along concave side 178 and convex side 179 are symmetrically aligned along their respective radius of curvature R" relative to the circular path that could be formed along arc A of implant 100. Accordingly, although the convex surface may have a length greater than the length of the concave surface, the number of roughened scallops may be equal. This may be done, in some embodiments, by spacing the scallops further apart on the convex side than on the concave side. Accordingly a line drawn normal to the curvature of the arc A may intersect and align with scallops on both the concave and convex sides. Alternatively, as seen in FIGS. 7C and 8C the locking surface 196 may be located along the sides extending between the concave and convex surfaces. Roughened scallops located along the sides extending between the concave and convex surfaces are positioned so that scallops are symmetrically spaced apart relative to their respective radius of curvature $R^1$-$R^5$ with respect to a circular path that could be formed by arc A of implant 100.

As will be described below, the roughened features of locking surface 196, such as the scallops, cooperate with the locking element 108 to secure the post at a desired height relative to the locker 104 and the base 102. In some embodiments, the scallops are closely spaced together to enable an incremental increase and decrease in the height of the implant along arc A. A scallop radius may substantially correspond with a radius of the locking element 108, providing a relatively tight fit when the locking element is engaged with the locking surface 196. In some embodiments, the locking surface 196 is not scalloped, but includes other roughening features. For example, in some embodiments the roughened features of the locking surface includes protruding triangular features or block-like features forming teeth. Still other surface features may be simply rough surfaces, such as those formed by shot peening, blasting, etching, or machining to increase the frictional properties of the locking surface 196. Still other roughened surface features are contemplated. In yet other embodiments, the locking surface 196 is relatively smooth, thereby allowing for an infinite number of expansion increments.

In addition to the features described above, the post 106 includes a flange 198. In the exemplary embodiment shown, the flange 198 includes instrument receiving grips 200 along its outer edges, formed to fit instruments during implantation or expansion.

Figure 9:
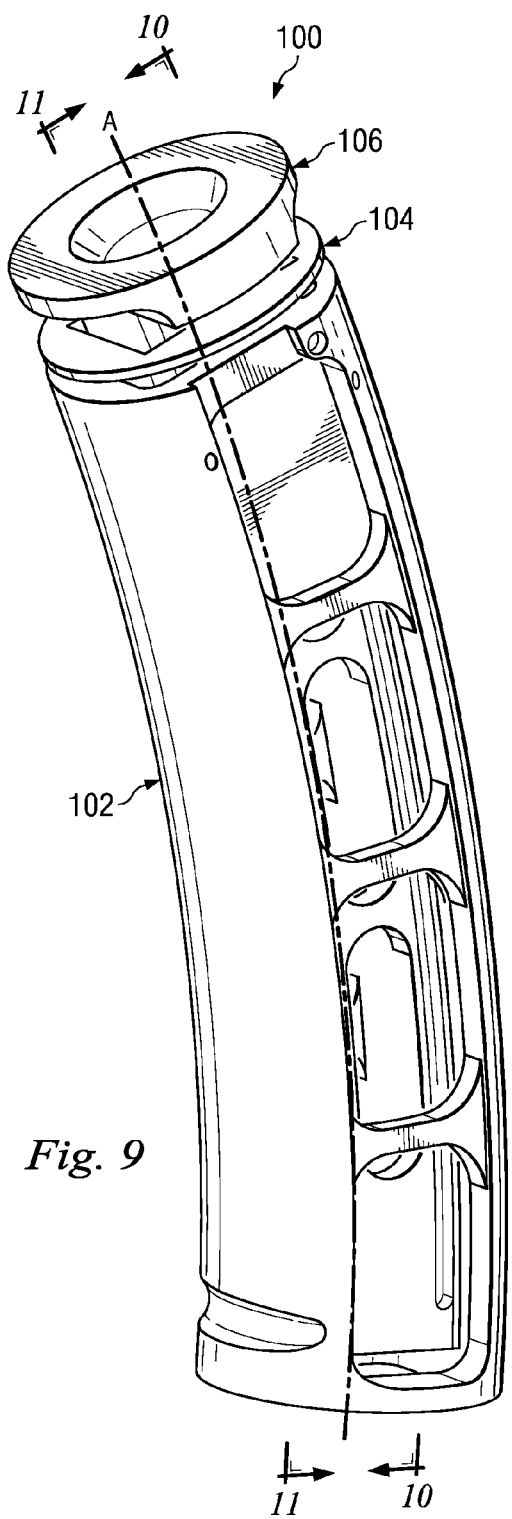
FIG. 9 is a side pictorial illustration of the implant of FIG. 2.
Figure 10:
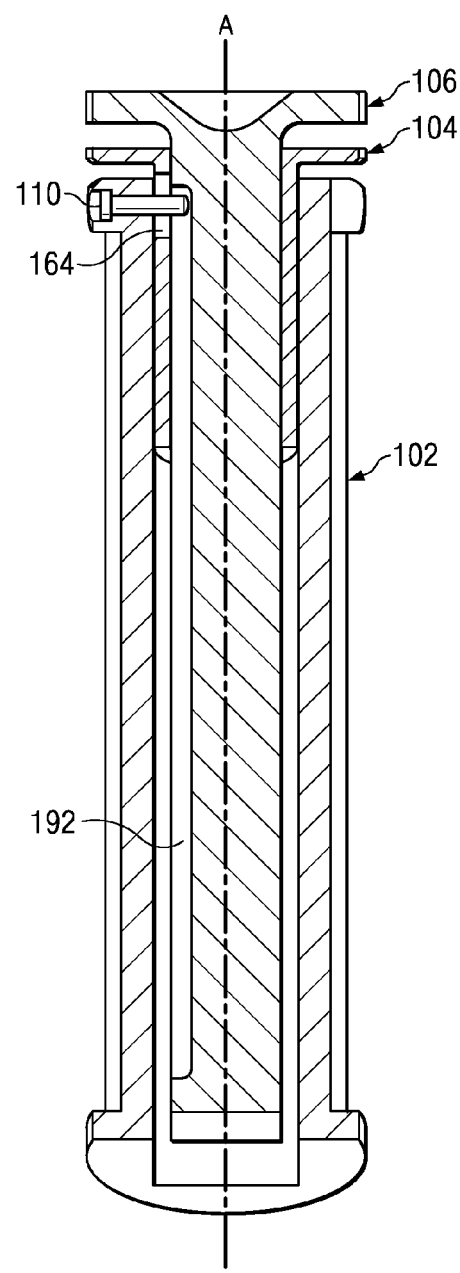
FIG. 10 is a sectional pictorial illustration taken along line 10-10 in FIG. 9.
Figure 11:
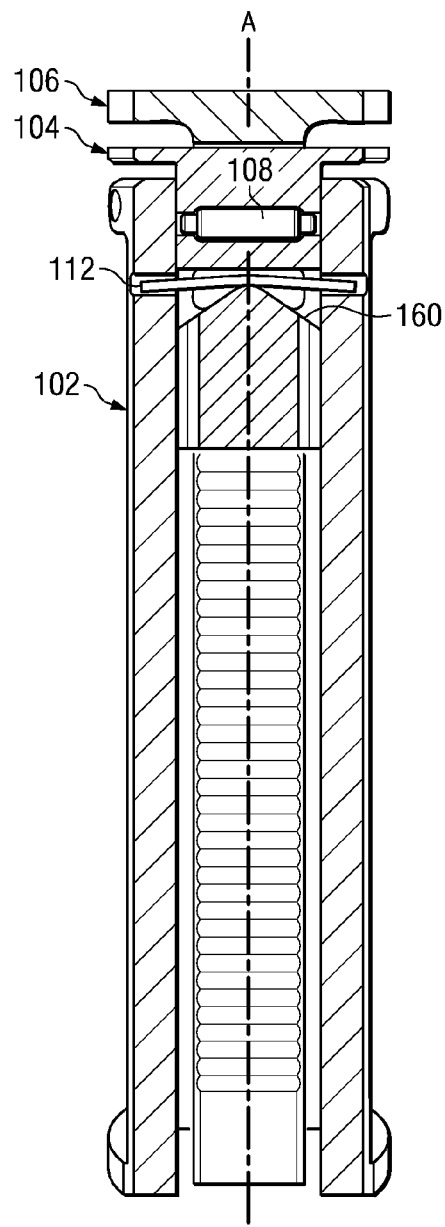
FIG. 11 is a sectional pictorial illustration taken along line 11-11 in FIG. 9.
Figure 12:
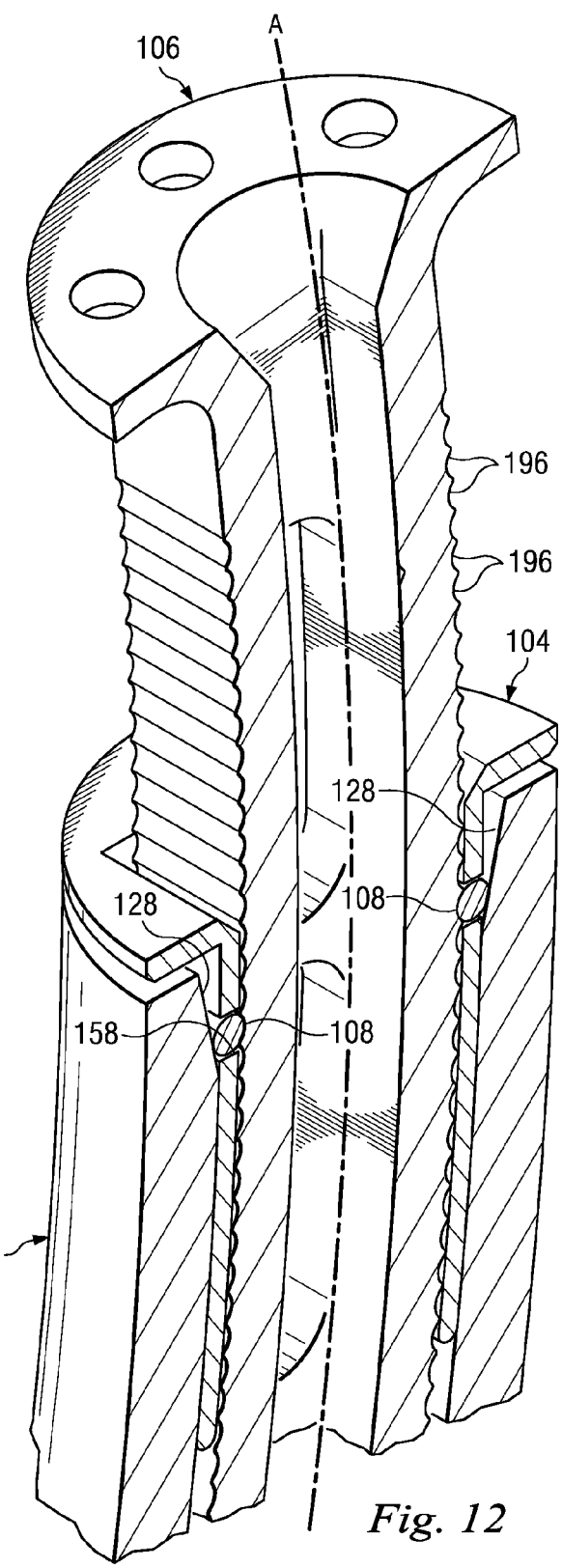
FIG. 12 is a sectional pictorial illustration of an exemplary locking arrangement usable with the implant of FIG. 2.

Operability of the implant 100 will be described with reference to FIGS. 9 through 12. FIG. 9 shows the implant 100 in an assembled condition. FIGS. 10 and 11 show cross-sectional views of the implant 100. FIG. 12 shows one model of components used to illustrate the functionality of the locking mechanism of the implant 100.

Referring now to the cross-sectional view in FIG. 10, the peg 110 is shown extending through the base 102, the locker 104, and into the post 106. As can be seen, the peg slot 164 in the locker 104 allows the locker 104 to move along arc A relative to the base 102. Likewise, the peg slot 192 in the post 106 allows additional movement of the post 106 relative to the base 102 along arc A. In this manner, the peg 110 may maintain the components of the implant 100 together, while at the same time allowing them to expand along arc A to increase and decrease the overall implant height.

FIG. 11 is a cross-sectional view through the biasing element 112 and through the locking element 108. The locking element 108 is maintained in its location by the locking element receiver 158 of the locker 104. As shown in FIG. 11, the biasing element 112 cooperates with the base 102 and the biasing member support 160 of the locker 104 to limit the axial movement of the locker 104 relative to the base 102. The biasing element 112 provides a continuous biasing force against the locker 104 to maintain the locker 104 in a position that locks the height of the implant.

FIG. 12 shows the relationship of the locking element 108 with the base 102, the locker 104, and the post 106, according to one embodiment of the implant. The locking element 108 is disposed in the locking element receiver 158, and protrudes through the receiver 158 such that the locking element 108 is selectively in contact with both the base 102 and the post 106.

In use, when the locker 104 is raised relative to the base 102, the locking element 108 is also raised relative to the base 102. Because the base 102 has a tapered section 128, upward movement of the locking element 108 relative to the base may provide free space for the locking element 108 to move away from the post 106. This may be referred to as an unlocked condition, allowing the post 106 to slide freely to either increase or decrease the overall height of the implant 100 along arc A. Once the desired height is achieved, the locker 104 may be moved downward relative to the base 102, wedging the locking element 108 between the tapered surface 128 of the base 102 and the post 106. So doing locks the overall height of the implant at its desired height. This may be referred to as a locked condition. The roughened surface features, such as the scallops, of the post 106 may provide a locking location for the locking element 108 and may reduce slippage between the locking element 108 and the post 106.

In the embodiment shown, the overall height of the implant 100 can be increased along arc A by raising the post 106 relative to the base 102. So doing may force the locking element 108 to move upwardly along the tapered section 128 to the unlocked condition, thereby allowing the implant height to be increased without requiring any separate attention to the locker 104. This also allows the locking element 108 to freely engage and disengage the roughened features of the locking surface 196. Accordingly, in some embodiments such as those shown having the scalloped surface features, during expansion, an audible clicking may be generated as the locking element 108 moves past and falls into each scalloped feature of the locking surface 196. In some embodiments, the locker 104 and the locking element 108 are configured to require manual or separate displacement of the locker 104 and the locking element 108 to reduce the overall height of the implant 100.

In the embodiment shown, the locking element 108 is a cylindrical rod that distributes its locking force over a wide surface area and in the embodiment shown over the entire width of the post 106. Accordingly, the locking element 108 contacts the post 106 along a contact line transverse to arc A of the implant 100, rather than at a single point. Because of this, the implant is less conducive to undesired slipping. It should be noted that the scalloped surface on the post 106 is optional and the post 106 may include other roughened features, indentations or elements that increase the friction between the locking element and the post or alternatively, may have a smooth surface.

In the embodiment shown, the implant 100 includes symmetrically locking features, including opposed tapered surfaces on the base 102, two locking elements 108 in two opposed receiving apertures 158, and two opposite locking surfaces 196. This symmetry may aid expansion and collapse of the implant by substantially equalizing the forces required at each side of the implant to expand or collapse it, providing a better level of control to the physician placing or removing the implant.

Figure 1A:
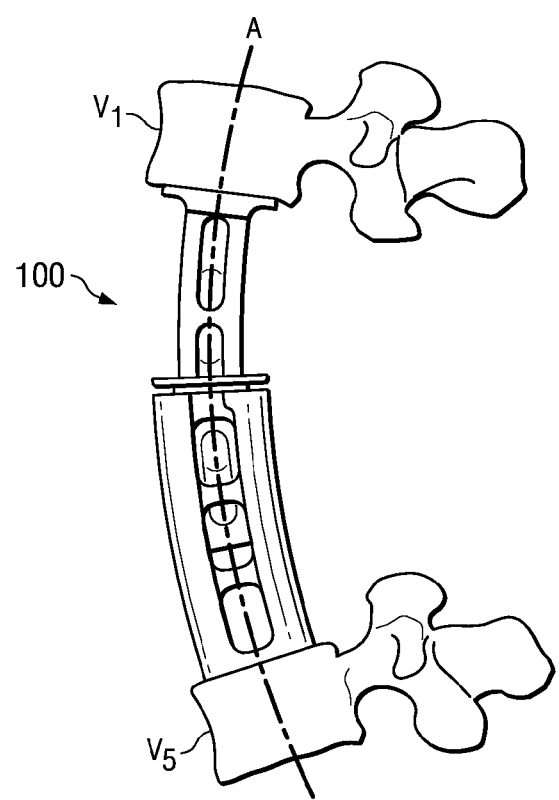
FIG. 1A is an illustration of an elevation view of a segment of a lumbar spine with an exemplary implant inserted between two vertebras.

During implantation, the implant 100 may be gripped with a surgical instrument at instrument receiving features of the base 102 and at the instrument receiving grips 200 of the post 106. In its smallest condition, the implant may be introduced to a patient through the smallest possible incision. In one exemplary embodiment, the implant 100 may be introduced between two bone structures, such as between vertebral bodies, such as the vertebral bodies V1 and V5 in FIG. 1A, replacing the vertebral bodies V2-V4 along with the discs D1-D4. Once positioned between the adjacent bone structures, the implant 100 may be distracted to increase the overall implant height along arc A to match the natural curvature of the spine as seen in FIG. 1A. Using the instruments, the post 106 is displaced along arc A relative to the base 102. In so doing, the post 106 frictionally acts on the locking element 108 to raise it relative to the base 102, along the tapered section 128. Once a desired height is achieved, the base 102 and post 106 are released. The continuous biasing force of the biasing member 112 acting on the locker 104 draws the locker 104 and the locking element 108 into a locking condition, where the locking element is wedged between the tapered section 128 and the locking surface 196 of the post 106. This compressive force locks the implant 100 against further decreases in the overall height. Once expanded, an implanting physician may introduce optional bone growth promoters into the base 102 or post 106 through the vascularization aperture 136 and the vascularization holes 194, respectively.

If it later becomes necessary to remove the implant, the locker flange 157 may be raised relative to the base 102 to remove the locking element 108 from its wedged position. Once the locking element 108 is free to disengage the locking surface 196 of the post 106, the post 106 may collapse into the locker 104, and the implant 100 may be removed from the patient. Again, although described with reference to one locking element, it is understood that two or more locking elements may be included to provide symmetry.

In the implantation method described above, some amount of the distraction force is used to overcome the biasing force of the biasing member 112. In some embodiments, the biasing member may be adjusted to provide a stronger biasing force to resist undesirable actuation of the implant once released. The stronger the biasing member, the greater the force required to deploy the device. However, in other implantation methods, the locker 104 may be separately raised relative to the base 102 to release the locking element prior to distracting the post 106 from the base 102. In this way, the complete distraction force may be used for distraction, rather than a portion being used to overcome the biasing force acting on the locker 104.

In yet other implantation methods, the implant may also be deployed by raising post 106 relative to the base 102 from the bottom end 182. In these embodiments, deploying instruments may attach to the post bottom end 182, such as at the bottom surface 183, or to features on the post 106 such as the vascularization apertures 194, and in addition, attach to the instrument receiving features 124 on the base 102. By moving the post 106 from the bottom end 182 (or the vascularization apertures 194) relative to the instrument receiving features 124, the distance between the bottom end 182 (or the vascularization apertures 194) and the instrument receiving features 124 decreases, while the overall height of the implant increases along arc A. Accordingly, during deployment, the gripping portions of the instrument move closer together (decreasing the instrument size), while the height of the implant increases along arc A. Because in this embodiment, the instrument does not grip at the ends of the implant, the implant can be deployed into a space or cavity where both ends of the implant are not directly accessible at the same time.

Figure 13:
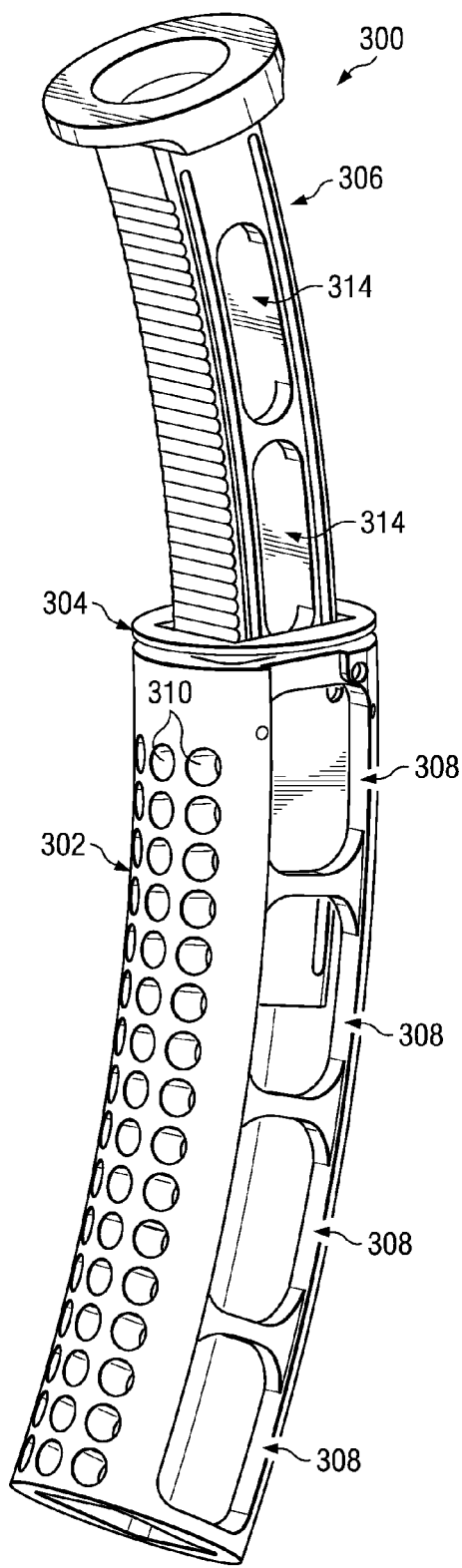
FIG. 13 is a pictorial illustration of an elevation view of another exemplary embodiment of the present invention.
Figure 14:
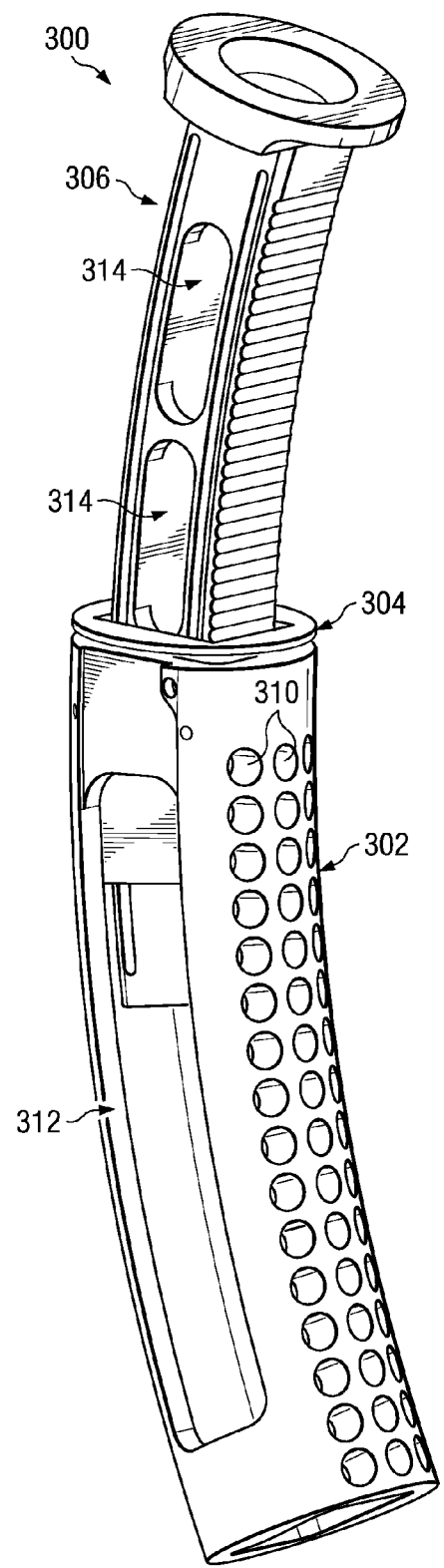
FIG. 14 is another pictorial illustration of an elevation view of the exemplary embodiment of FIG. 13.

FIGS. 13 and 14 show an embodiment of another exemplary expandable implant 300 having additional vascularization openings. FIG. 13 shows a back side and FIG. 14 shows a front side. The implant 300 is similar to the implant 100 described above, including a base 302, a locker 304, and a post 306. In this embodiment, the heights of the base 302 and the post 306 are greater than those of the base 102 and post 106 described above. To accommodate grafting, tissue, or other material, the implant 300 includes rear vascularization openings 308, side vascularization openings 310, and at least one front access window 312. The rear and side openings 308, 310, as well as the access window 312, increase the porosity of the implant, promoting breathability and bone growth. The access window 312 is larger than the rear and side openings 308, 310 and provides access to the interior of the base 302. Accordingly, during implantation, a physician may introduce grafting material through the access window 312 to pack grafting material, tissue, or other material into the base 302. The larger size of the access window 312 simplifies the packing process, while the smaller size of the rear and side openings 308, 310 help reduce the opportunity for the material being packed to extrude from the rear or side openings. This may become important when the implant 300 is placed in a spine and the rear of the implant 100 is facing or located adjacent the spinal cord. Similarly, the larger size of the access window 312 may allow placement of large segments of grafting, tissue, or other material, while the smaller rear and side openings 308, 310 help contain the large segments within the base 302. The post 306 of the implant 300 also includes vascularization holes 314 similar to the vascularization holes 194 described above.

Figure 15:
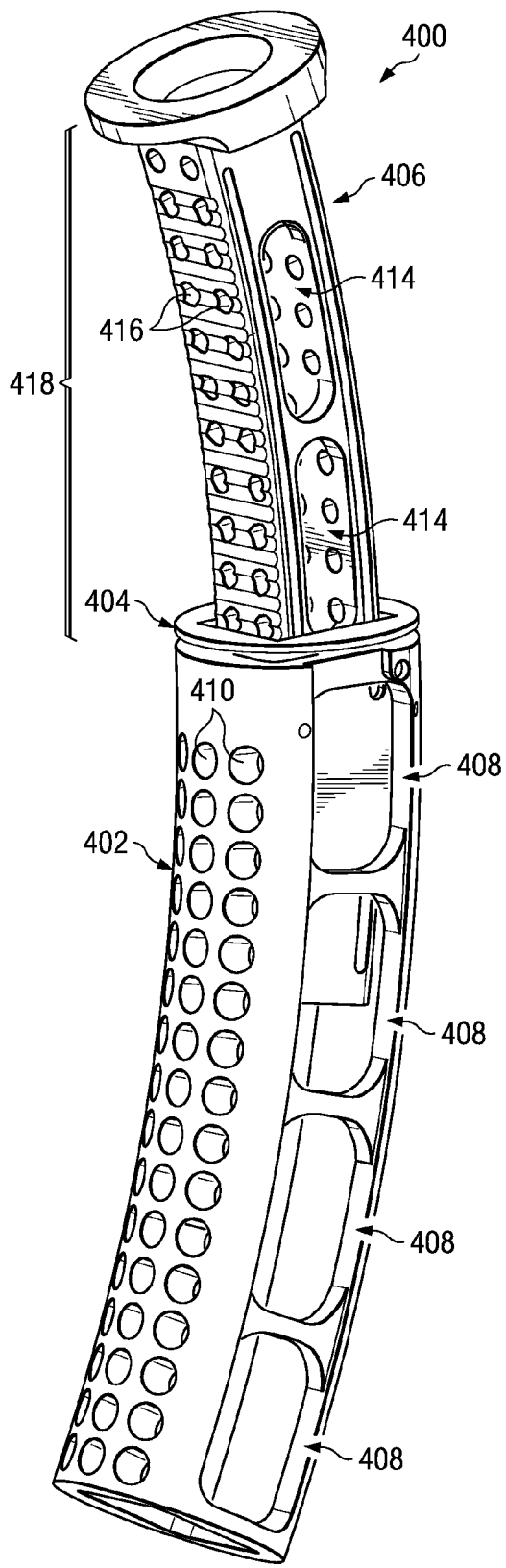
FIG. 15 is a pictorial illustration of an elevation view of another exemplary embodiment of the present invention.
Figure 16:
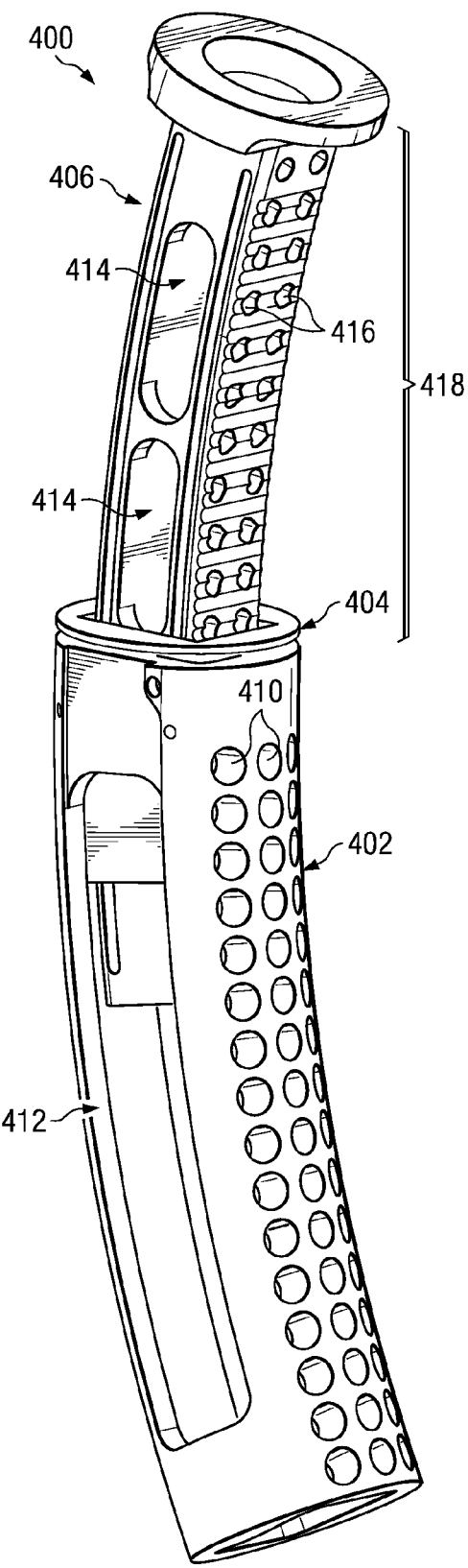
FIG. 16 is another pictorial illustration of an elevation view of the exemplary embodiment of FIG. 15.

FIGS. 15 and 16 show another embodiment of an exemplary expandable implant 400. FIG. 15 shows a back side and FIG. 16 shows a front side. Again, the implant 400 is similar to the implant 100 described above, including a base 402, a locker 404, and a post 406. To accommodate grafting, tissue, or other material, the implant 400 includes rear vascularization openings 408, side vascularization openings 410, and front access windows 412 that increase the porosity of the implant, promoting breathability and bone growth. As described above, the access window 412 is larger than the rear and side openings 408, 410 and provides access to the interior of the base 402. In this embodiment, the rear openings 408 are larger than the side openings 410. Nevertheless, in this embodiment, the rear openings 408 are smaller than the access window 412. As can be seen, in this embodiment, the base 402 includes three rear openings 408.

The post 406 of the implant 400 also includes vascularization holes 414 similar to the vascularization holes 194 described above. In addition, the post 406 includes post openings 416 in a locking surface 418. The locking surface 418 may be similar to the locking surface 196 described above. The post openings 416 provide additional vascularization to the implant 400.

In the embodiments shown in FIGS. 13-16, the implants include only one access window. However, in other embodiments, the implants include more than one access window on the front side, while the rear and side openings are still maintained smaller than the front access windows. In other embodiments, the rear openings are smaller than the side openings. It also should be noted that the implant may include more or less than three rear openings, and the size of the openings may be determined in part based upon the size of the implant and based upon the size or amount of packing material anticipated.

While the post has been shown as telescopically received within the locker and the base relative to arc A, it will be appreciated that in a further embodiment the respective configuration is inverted such that a portion of the base is received within the post. Moreover, while a substantially cylindrical structure having rectangular bores has been shown for the purposes of illustration, in alternative embodiments the tubular and rectangular shapes may take the form of a rectangle, square, ellipse, diamond, oval, D-shape or any shape desired to conform and substantially match the adjacent bone or the bone structure that is being replaced. As a result, the definition of tubular is not intended to be limited to cylindrical but is instead intended to cover all components that may be utilized to reduce the present invention.

While the present device has been described with respect to insertion between multiple vertebrae after removal of the intervening vertebrae and intervertebral disc, it is contemplated that the length of the device may be sized appropriate to span at least one vertebra to multiple vertebrae. Additionally, the device may find application in other orthopedic areas and the size and shape of the device may be made to substantially match the implantation site. For example, while the present embodiment has been illustrated as a substantially cylindrical device, it is contemplated that in certain spinal applications it is desirable that the device have a substantially D shaped cross-section as viewed from top to bottom such that the anterior portion of the device has an exterior convexly curved surface matching the anterior of the vertebral body while the posterior portion of the device is substantially flat or concave allowing it to be positioned closer to the spinal canal without protruding into the spinal canal.

Figures 17A, 17B:
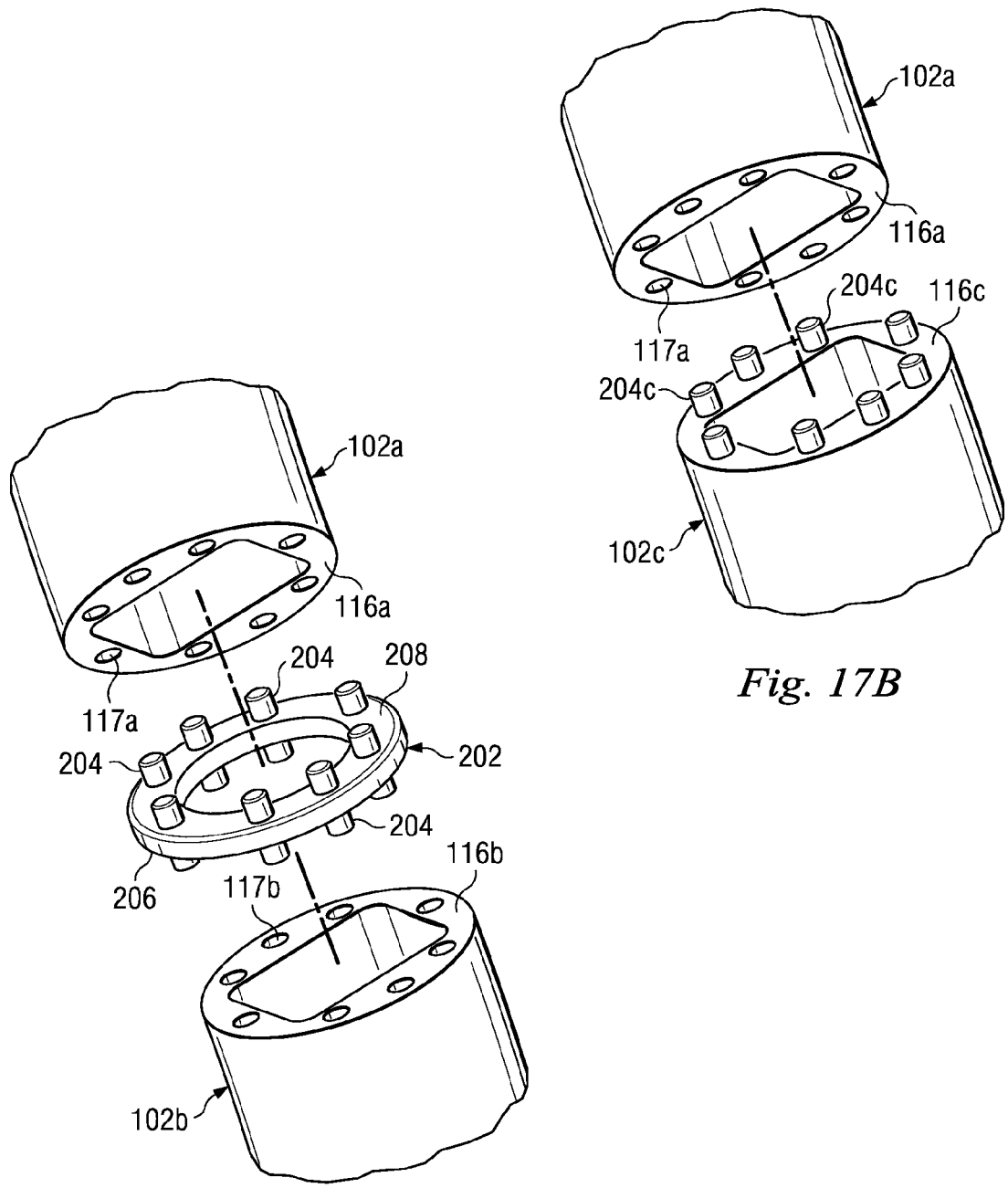
FIG. 17A is an isometric pictorial illustration of an exemplary base component and another exemplary base component with a coupling member disposed therebetween to couple the base components together.
FIG. 17B is an isometric pictorial illustration of an exemplary base component and another exemplary base component with projections to couple the base components together.

In an alternative embodiment, two expandable implants such as the implants 100 may be coupled together to form a longer implant, so that the length of the coupled implants may be sized appropriately to span multiple vertebrae. As seen in FIG. 17A, the respective base 102a and 102b of each expandable implant 100 has bottom surface 116a and 116b that contains recesses 117a and 117b. The recesses 117a and 117b are contoured to receive an exemplary coupling member 202 that connects the bases 102a and 102b together. Coupling member 202 has projections 204 on a top surface 206 and a bottom surface 208 that correspond to the pattern of recesses 117a and 117b on the respective bases 102a and 102b. The two bases are coupled by positioning the coupling member 202 between the two bottom surfaces 116 of the respective bases 102a and 102b so that the projections 204 align with the recesses 117. Once the coupling member 202 is properly positioned and inserted between the respective bottom surfaces 116, the recesses 117 and projections 204 are coupled together by press fitting, ultrasonically welding, using adhesive material, click fitting, friction fitting, or other means that would be apparent to one skilled in the art. Although disclosed as a couple for two bases, it is contemplated that in alternative embodiments, the coupling member may connect two posts or a post of one implant to a base of another implant or alternatively, to a different implant altogether.

FIG. 17B shows another alternative embodiment, two expandable implants 100 coupled together to form a longer implant, so that the length of the coupled implants may be sized appropriately to span multiple vertebrae. Here, the respective base 102a of one expandable implant 100 has bottom surface 116a that contains recesses 117a. The respective base of the other expandable implant 100 has a bottom surface 116c that contains projections 204c. The recesses 117a are contoured to receive the projections 204. The two bases are coupled by positioning the two bottom surfaces 116 relative to one another so that the projections 204c align with the recesses 117a. Once the bases are properly aligned with one another, the recesses 117a and projections 204c are coupled together by press fitting, ultrasonically welding, using adhesive material, click fitting, friction fitting, or other means that would be apparent to one skilled in the art. Although disclosed as a couple for two bases, it is contemplated that in alternative embodiments, the coupling may connect two posts or a post of one implant to a base of another implant or alternatively, to a different implant altogether.

Figure 18:
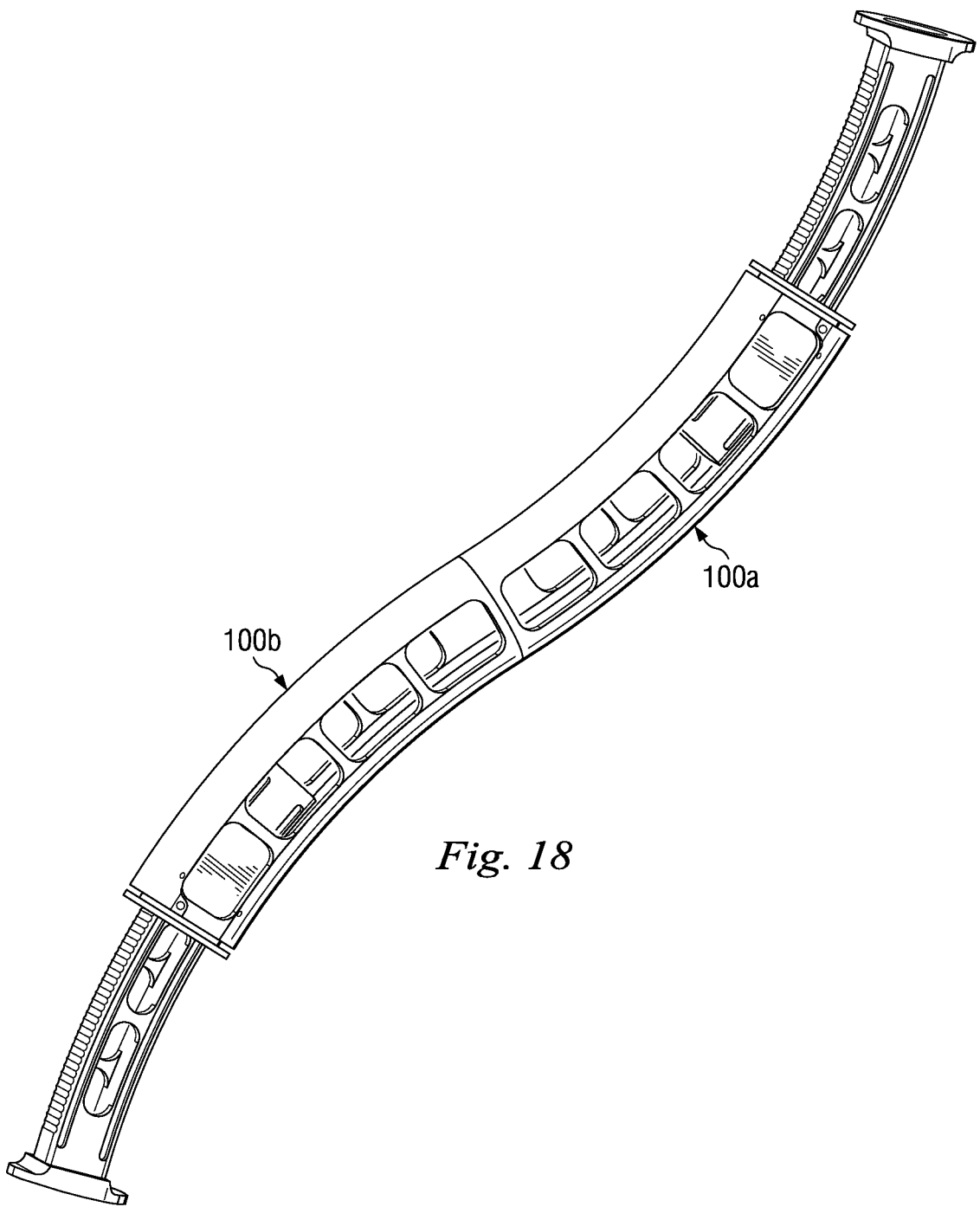
FIG. 18 is a pictorial illustration of an elevation view of another exemplary embodiment of the present invention where two exemplary implants of FIG. 2 are coupled together.
Figure 19:
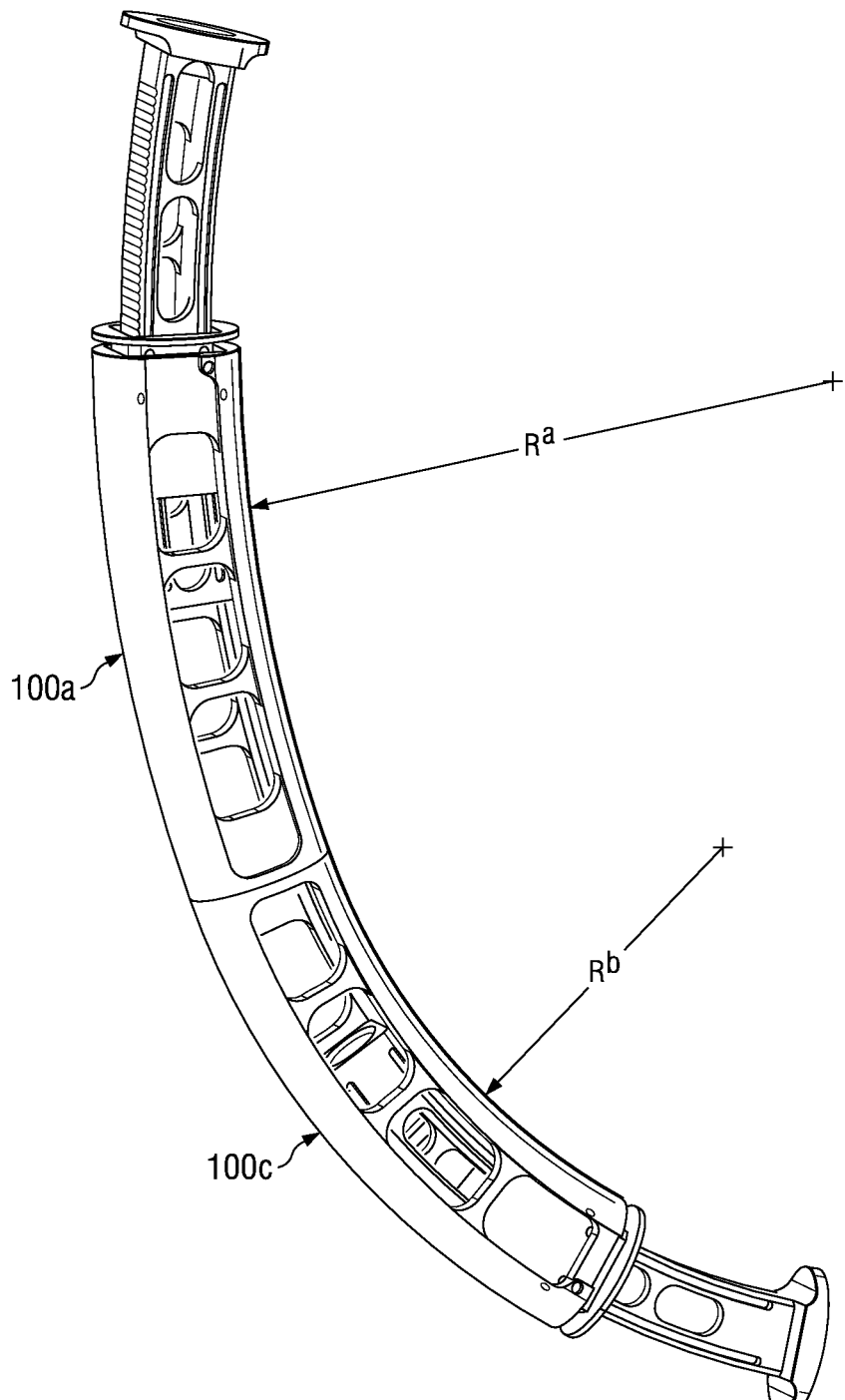
FIG. 19 is a pictorial illustration of an elevation view of another exemplary embodiment of the present invention where one exemplary implant is coupled to another exemplary implant where the two implants have different radii of curvatures.

FIGS. 18 and 19 display alternative embodiments where two expandable implants are coupled together as described above. Referring to FIG. 18, first and second expandable implants 100a and 100b have been coupled together where the first implant 100a has a base, locker, and post whose concave sides are anteriorly facing and the second implant 100b has a base, locker, and post whose concave sides are posteriorly facing. Such coupled implants are suitable to be positioned along the throacolumbar juncture to support the kyphotic and lordotic curves that are natural for this region of the spine.

Alternatively to the arrangement displayed in FIG. 18, the two implants 100a and 100b can be coupled together so that the concave curvatures of their respective base, locker, and post face the same direction when inserted into the spine. If such coupled implants are inserted into the spine with their concave sides facing anteriorly the coupled implants would have a kyphotic curve and thereby be able to support a large spinal region having a kyphotic curve. By contrast, if such coupled implants are inserted into the spine with their concave sides facing posteriorly the coupled implants would have a lordotic curve and thereby be able to support a large spinal region having a lordotic curve.

In an alternative embodiment, two implants could be coupled together where the two implants have differing radii of curvature. Referring to FIG. 19, two expandable implants 100 have been coupled together via the method described above. Expandable implant 100a has a radius of curvature $R^a$. Expandable implant 100c has a radius of curvature $R^b$.

Expandable implant 100*a* has a larger radius of curvature than expandable implant 100*c*. Coupling implants 100*a* and 100*c* having different radii of curvature allows the coupled implants to better adapt to certain portions of the human spine. For example, the lumbar region of the spine has an overall lordotic shape, but the upper portion of the lumbar region has a different radius of curvature than the lower portion. Such joined implants 100*a* and 100*c* as shown in FIG. 19, where the respective implants have different radius of curvature, would be suited to support the varying lordotic curve found within the lumbar region of the spine.

Although the coupling of implants discussed above involved two implant, it is anticipated that more than two expandable implants 100 can be joined to form various combinations of lengths and curvatures. Furthermore, the above description of combinations of lengths and curvatures for two or more expandable implants 100 is not intended to be limiting as other combinations based on the above description are contemplated.

The implant 100 is described as being somewhat porous with vascularization apertures 136, 162, and 190. The vascularization apertures 136, 162, and 190 of the base 102, locker 104, and post 106 respectively, may be formed using any suitable method, but here, are described as being formed through an end milling process. As shown in FIG. 20 with respect to base 102, when vascularization aperture 136*a* is formed the end mill is drilled to a depth measuring X as shown in FIG. 20. Additionally, the end mill leaves support bars 137*a* extending between the concave side 140 and convex side 142 of the base 102 on the top and bottom portion of vascularization aperture 136*a*. Similar to vascularization aperture 136*a*, vascularization aperture 136*b* is formed by using an end mill to drill to a depth measuring X leaving support bars 137*b* as shown in FIG. 20. However, when vascularization aperture 136*b* is formed on the opposing side of base 102 from vascularization 136*a* the end mill is positioned such that it would overlap the support bar 137*a* on the opposing vascularization aperture 136*a* if allowed to drill completely through to the opposing side of base 102. The described end milling process creates vascularization apertures 136*a* and 136*b* on opposing sides that are offset from one another and have equal drilling depth X within the base thereby creating overlapping vascularization apertures with the same aperture depth along the sides of base 102. Because the end milling process creates overlapping vascularization apertures 136*a* and 136*b* with the same aperture depth X within base 102, the end mill indirectly forms a lumen or bore 122 within the interior of base 102. Thus, the end milling technique described allows one skilled in the art to form a lumen or bore within a curved shaped object such as base 102.

The end milling technique described above with reference to base 102 may also be used to form the vascularization apertures for the locker 104 and post 106 and their respective bore or lumen.

Figure 22:
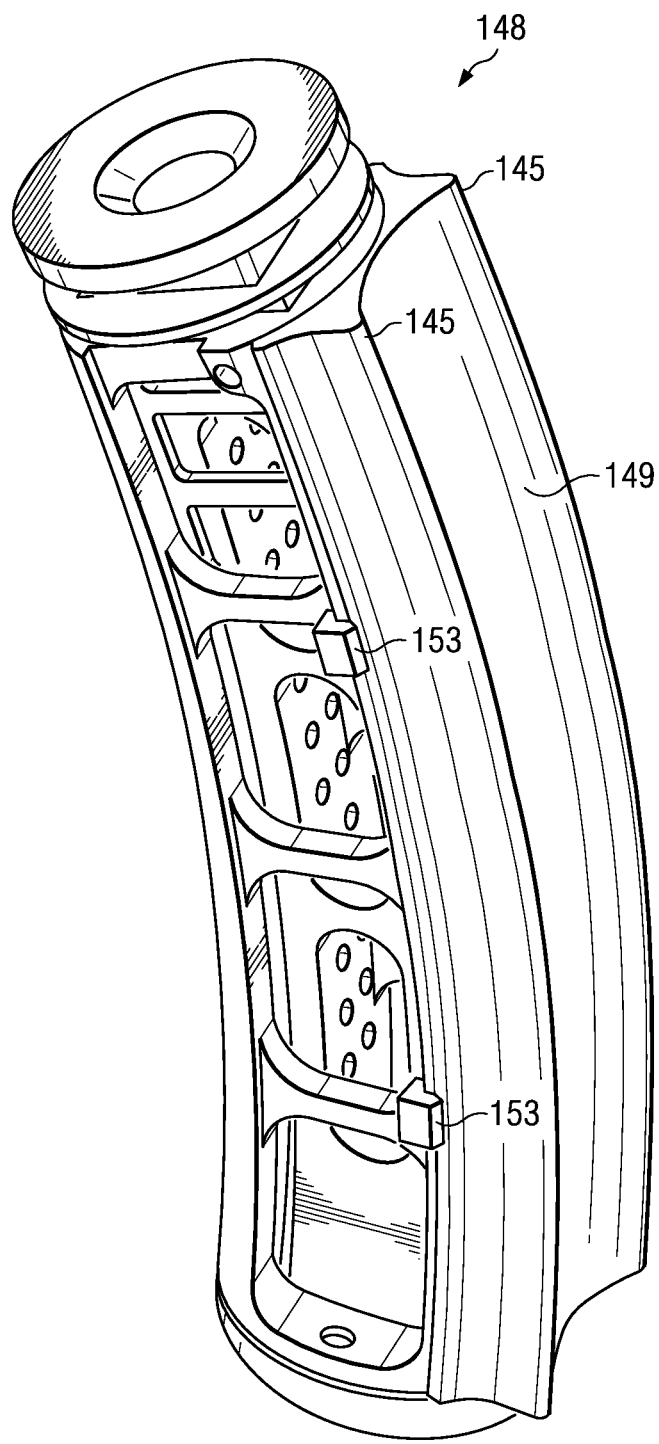
FIG. 22 is a pictorial illustration of an exemplary guard component attached to the implant of FIG. 2.

A guard 148, as seen in FIG. 21, may be attached to expandable implant 100. The guard may provide an interface between the expandable implant 100 and surrounding anatomy within the spinal region. The guard 148 may be configured to match the contour of the expandable implant 100 and the corresponding curvature of the spine as seen in FIGS. 21 and 22. Thus, guard 148 may be placed along any side, length, and/or curvature of expandable implant 100. The guard 148 may have lateral peaks or rounded edges 145 that provide lateral support to the surrounding anatomy. For example, rounded edges 145 may help to prevent the dura and blood vessels that are present within the spinal region from moving laterally outside of the rounded edges 148 in order to protect these anatomical objects. The guard 148 is attached to expandable implant 100 by coupling 153 as seen in FIG. 22. Specifically coupling 153 includes a first portion 151 extending out from implant 100 and a second portion 147 extending transverse to first portion 151. The first portion 151 and second portion 147 of coupling 153 form a recess that allows the guard to attach to implant 100. Attachment of guard 148 to expandable implant 100 can occur before or after implantation. In some embodiments, the guard 148 has a trough 149 recessed between outwardly extending rounded edges 145; the trough has a smooth, and ubiquitous surface that helps to eliminate irritation and damage to the surrounding dura matter and blood vessels that are present within the spinal region. The guard 148 may be made of materials that are resorbable to avoid a second surgery to remove guard 148.

Embodiments of the implant in whole or in part may be constructed of biocompatible materials of various types. Examples of implant materials include, but are not limited to, non-reinforced polymers, carbon-reinforced polymer composites, PEEK and PEEK composites, shape-memory alloys, titanium, titanium alloys, cobalt chrome alloys, stainless steel, ceramics and combinations thereof. In some embodiments, the locking elements 108 are formed or cobalt chrome and the base 102, locker 104, and post 106 are formed of titanium.

If the implant is made from radiolucent material, radiographic markers can be located on the implant to provide the ability to monitor and determine radiographically or fluoroscopically the location of the implant in the spinal disc space. In some embodiments, radiographic markers are placed to show the location of the locking elements relative to the post and base.

In some embodiments, the implant or individual components of the implant are constructed of solid sections of bone or other tissues. In other embodiments, the implant is constructed of planks of bone that are assembled into a final configuration. The implant may be constructed of planks of bone that are assembled along horizontal or vertical planes through one or more longitudinal axes of the implant. In some embodiments, a cavity is cut or constructed through the implant. The cavity may be useful to contain grafting materials. Tissue materials include, but are not limited to, synthetic or natural autograft, allograft or xenograft, and may be resorbable or non-resorbable in nature. Examples of other tissue materials include, but are not limited to, hard tissues, connective tissues, demineralized bone matrix and combinations thereof. Examples of resorbable materials that may be used include, but are not limited to, polylactide, polyglycolide, tyrosine-derived polycarbonate, polyanhydride, polyorthoester, polyphosphazene, calcium phosphate, hydroxyapatite, bioactive glass, and combinations thereof. Implant may be solid, porous, spongy, perforated, drilled, and/or open.

In some circumstances, it is advantageous to pack all or a portion of the interior and/or periphery of the implant with a suitable osteogenetic material or therapeutic composition. Osteogenic materials include, without limitation, autograft, allograft, xenograft, demineralized bone, synthetic and natural bone graft substitutes, such as bioceramics and polymers, and osteoinductive factors. A separate carrier to hold materials within the device can also be used. These carriers can include collagenbased carriers, bioceramic materials, such as BIOGLASS®, hydroxyapatite and calcium phosphate compositions. The carrier material may be provided in the form of a sponge, a block, folded sheet, putty, paste, graft material or other suitable form. The osteogenetic compositions may include an effective amount of a bone morphogenetic protein, transforming growth factor β1, insulin-like growth factor 1, platelet-derived growth factor, fibroblast growth factor, LIM mineralization protein (LMP), and combinations thereof or other therapeutic or infection resistant agents, separately or held within a suitable carrier material. A technique of an embodiment of the invention is to first pack the interior of an unexpanded implant with material and then place one or both end members if desired.

Access to the surgical site may be through any surgical approach that will allow adequate visualization and/or manipulation of the bone structures. Example surgical approaches include, but are not limited to, any one or combination of anterior, antero-lateral, posterior, postero-lateral, transforaminal, and/or far lateral approaches. Implant insertion can occur through a single pathway or through multiple pathways, or through multiple pathways to multiple levels of the spinal column. Minimally invasive techniques employing instruments and implants are also contemplated.

It is understood that all spatial references, such as "top," "inner," "outer," "bottom," "left," "right," "anterior," "posterior," "superior," "inferior," "medial," "lateral," "upper," and "lower" are for illustrative purposes only and can be varied within the scope of the disclosure.

While embodiments of the invention may be applied to the lumbar spinal region, embodiments may also be applied to the cervical or thoracic spine or between other bone structures. Expandable implant 100 may also be useful in replacing long bones or portions of appendages such as the legs and arms, or a rib or other bone that is generally longer than it is wide. Examples include, but are not limited to, a femur, tibia, fibula, humerus, radius, ulna, phalanges, clavicle, and any of the ribs.

While embodiments of the invention have been illustrated and described in detail in the disclosure, the disclosure is to be considered as illustrative and not restrictive in character. All changes and modifications that come within the spirit of the invention are to be considered within the scope of the disclosure.

What is claimed is:

1. An expandable medical implant for supporting bone structures, the implant comprising:
    an outer member having a first side and an opposing second side extending along a mid-line, the first side having a first curvature along the mid-line and the second side having a second curvature along the mid-line, the first side being longer than the second side, the outer member having a first height;
    an inner member having a third side and an opposing fourth side, the third side having a third curvature and the fourth side having a fourth curvature, the third side being longer than the fourth side, the inner member having a second height, the inner member being receivable in the outer member and movable relative to the outer member along an arc bounded by the first curvature and the second curvature of the outer member thereby increasing or decreasing an overall height of the implant defined by the outer member's first height and a portion of the inner member's second height;
    wherein the outer member includes a tapered surface and the inner member includes a roughened locking surface including a series of roughening scallops; and
    a locker member disposed between the inner member and the outer member such that the roughened locking surface is spaced apart from an inner surface of the outer member, the locker member including a receiving aperture containing a locking element being disposed between the tapered surface and the roughened locking surface that is movable between a locked position engaging the tapered surface and one of the roughening scallops to inhibit a decrease in the overall height of the implant and an unlocked position permitting at least an increase in the overall height of the implant.

2. The expandable implant of claim 1, wherein the outer member is configured to cooperatively engage a first bone structure and the inner member is configured to cooperatively engage a second bone structure.

3. The expandable implant of claim 1, wherein the locker member is configured to act on the locking element to affect the position of the locking element relative to the tapered surface, and wherein the tapered surface is configured to affect the position of the locking element relative to the roughened locking surface.

4. The expandable implant of claim 1, wherein the locker member and the locking element are movable relative to the tapered surface between the locked condition and the unlocked condition.

5. The expandable implant of claim 4, further including a biasing member configured to bias the locker member toward the locked condition.

6. The expandable implant of claim 1, including two locking elements disposed between the inner and outer members at opposing ends of the inner member.

7. The expandable implant of claim 2, wherein the outer member has a first endplate surface configured to cooperatively engage the first bone structure and the inner member has a second endplate surface configured to cooperatively engage the second bone structure.

8. The expandable implant of claim 1, wherein at least one of the inner member and the outer member includes vascularization openings formed on opposing sides of the implant and wherein the vascularization openings on one of the opposing sides are larger than the vascularization openings on the other of the opposing sides.

9. The expandable implant of claim 1, wherein the outer member is configured to cooperatively engage one of a coupling member and another expandable implant.

10. The expandable implant of claim 1, wherein an outer surface of the locker member has a length extending between first and second ends of the locker member, wherein a majority of the length of the outer surface of the locker member engages the inner surface of the outer member when the locker member is disposed between the tapered surface and the roughened locking surface.

11. A method of supporting vertebrae with an expandable medical implant, the method comprising:
    gaining surgical access to a curved portion of the spinal column;
    removing one or more vertebras to form a vertebral gap;
    providing the implant of claim 1;
    displacing the inner member relative to the outer member to a height approximating the natural height of the vertebral gap;
    moving the locking mechanism to the locked position to retain the height of the implant; and
    positioning the implant in the spinal column oriented to approximate the height and curvature of the one or more removed vertebra.

12. The method of claim 11, wherein said moving is performed before said positioning.

13. The method of claim 11, wherein said positioning is performed before said moving.

14. An expandable medical implant for supporting bone structures, the implant comprising:

an outer member having a first end surface defining a first plane, the first end surface being configured to cooperatively engage a first bone structure;

an inner member having a second end surface defining a second plane, the second end surface being configured to cooperatively engage a second bone structure, the inner member being receivable in the outer member and movable relative to the outer member along a curved path between a first position and a second position wherein the second position is an expanded position;

wherein the second plane intersects the first plane at a first angle when the inner member is in the first position;

wherein the second plane intersects the first plane at a second angle when the inner member is in the second position;

wherein the outer member includes a tapered surface and the inner member includes a roughened locking surface including a series of roughening scallops;

a locking member disposed between the outer and inner members having a flange and a locking element disposed between the tapered surface and the roughened locking surface, the roughened locking surface being spaced apart from an inner surface of the outer member, the locking element being movable between a locked position engaging the tapered surface and one of the roughening scallops that inhibits an increase in the first angle and an unlocked position permitting an increase from at least the first angle to the second angle.

15. The expandable implant of claim 14, wherein the second angle is greater than the first angle.

* * * * *